United States Patent [19]
Hillman et al.

[11] Patent Number: 5,871,973
[45] Date of Patent: Feb. 16, 1999

[54] CELL DIVISION REGULATORS

[75] Inventors: Jennifer L. Hillman; Olga Bandman, both of Mountain View; Preeti Lal; Purvi Shah, both of Sunnyvale; Neil C. Corley, Mountain View, all of Calif.

[73] Assignee: Incyte Pharmaceuticals, Inc., Palo Alto, Calif.

[21] Appl. No.: 951,148

[22] Filed: Oct. 15, 1997

[51] Int. Cl.$^6$ .......................... C12N 15/09; C07K 14/435
[52] U.S. Cl. ................ 435/69.1; 435/252.3; 435/252.33; 435/254.11; 435/254.3; 435/325; 435/410; 435/320.1; 530/350; 536/23.1; 536/23.5
[58] Field of Search ................................ 435/69.1, 252.3, 435/252.33, 254.11, 254.3, 325, 410, 320.1; 530/350; 536/23.1, 23.5

[56] References Cited

PUBLICATIONS

Prelich, G. et al., "Functional identity of proliferating cell nuclear antigen and a DNA polymerase–δ auxiliary protein", *Nature*, 326: 517–520 (1987).

Coxon, A. et al., "Fission yeast cdc21$^+$ belongs to a family of proteins involved in an early step of chromosomes replication", *Nucleic Acids Res.*, 20: 5571–5577 (1992).

Radomski, N. et al., "Molecular Cloning of a Murine cDNA Encoding a Novel Protein, p38–2G4, Which Varies with the Cell Cycle", *Exp. Cell Res.*, 220: 434–445 (1995).

Mori, T. et al., "Isolation and mapping of a human gene (DIFF6) homologous to yeast CDC3, CDC10, CDC11, and CDC12, and mouse Diff6", *Cytogenet. Cell Genet.*, 73: 224–227 (1996).

Longtine, M.S. et al. "The septins: roles in cytokinesis and other processes", *Curr. Opin. Cell Biol.*, 8: 106–119 (1996).

Nagase, T. et al., "Prediction of the Coding Sequences of Unidentified Human Genes. VI. The Coding Sequences of 80 New Genes (KIAA0201–KIAA0280) Deduced by Analysis of cDNA Clones from Cell Line KG–1 and Brain", *DNA Res.*, 3: 321–329 (1996).

Saraste, M. et al., "The P–loop –a common motif in ATP– and GTP–binding proteins", *Trends Biochem. Sci.*, 15: 430–434 (1990).

Kato, K., (Direct Submission), GenBank Sequence Database (Accession 51203), National Center for Biotechnology Information, National Library of Medicine, Bethesda, Maryland, 20894 (GI 51203). No Year.

Kato, K., (Direct Submission), GenBank Sequence Database (Accession X61452), National Center for Biotechnology Information, National Library of Medicine, Bethesda, Maryland, 20894 (GI 51202). No year.

Ware, J. et al., (Direct Submission), GenBank Sequence Database (Accession 1809317), National Center for Biotechnology Information, National Library of Medicine, Bethesda, Maryland, 20894 (GI 1809317). No Year.

Ware, J. et al., (Direct Submission), GenBank Sequence Database (Accession U74628), National Center for Biotechnology Information, National Library of Medicine, Bethesda, Maryland, 20894 (GI 1809316). No Year.

Kato, K., (Direct Submission), GenBank Sequence Database (Accession 1469179), National Center for Biotechnology Information, National Library of Medicine, Bethesda, Maryland, 20894 (GI 1469179). No Year.

Nagase, T. et al., (Direct Submission), GenBank Sequence Database (Accession D50918), National Center for Biotechnology Information, National Library of Medicine, Bethesda, Maryland, 20894 (GI 1469178). No Year.

Nakagawa, Y. et al., (Direct Submission), GenBank Sequence Databse (Accession 1167967), National Center for Biotechnology Information, National Library of Medicine, Bethesda, Maryland, 20894 (GI 1167967). No year.

Nakagawa, Y. et al., (Direct Submission), GenBank Sequence Database (Accession U43918), National Center for Biotechnology Information, National Library of Medicine, Bethesda, Maryland, 20894 (GI 1167966). No Year.

Ware,J. and Zieger,B. Alternative expression of platelet glycoprotein Ib(beta) mRNA from an adjacent 5' gene with an imperfect polyadenylation signal sequence J. Clin. Invest. 99(3), 520–525 (Feb. 1, 1997).

*Primary Examiner*—Keith D. Hendricks
*Assistant Examiner*—Bradley S. Mayhew
*Attorney, Agent, or Firm*—Incyte Pharmaceuticals, Inc.

[57] ABSTRACT

The invention provides three human cell division regulators (HCDR) and polynucleotides which identify and encode HCDR. The invention also provides expression vectors, host cells, agonists, antibodies and antagonists. The invention also provides methods for preventing and treating disorders associated with expression of HCDR.

11 Claims, 26 Drawing Sheets

```
5' NNT GGG GTG GGG AAG GAC ATT CCA CAG GCT TTT TTG GCC CCT AGA GAC AGA
   9                18               27               36               45            54

AGG GGG TCA AAG AGA AAG GGA GAG CAA GCC AGG AAG CCA GAC AAC AAC AGC
   63               72               81               90               99           108

ATC AAA ACA AGG CTG TTT CTG TGT GTG AGG AAC TTT GCC TGG GAG ATA AAA TTA
   117              126              135              144              153          162

GAC CTA GAG CTT TCT GAC AGG GAG TCT GAA GCG TGG GAC ATG GAC CGT TCA CTG
   171              180              189              198              207          216
                                                         M   D   R   S   L

GGA TGG CAA GGG AAT TCT GTC CCT GAG GAC AGG ACT GAA GCT GGG ATC AAG CGT
   225              234              243              252              261          270
    G   W   Q   G   N   S   V   P   E   D   R   T   E   A   G   I   K   R

TTC CTG GAG GAC ACC ACG GAT GAT GGA GAA CTG AGC AAG TTC GTG AAG GAT TTC
   279              288              297              306              315          324
    F   L   E   D   T   T   D   D   G   E   L   S   K   F   V   K   D   F

TCA GGA AAT GCG AGC TGC CAC CCA CCA GAG GCT AAG ACC TGG GCA TCC AGG CCC
   333              342              351              360              369          378
    S   G   N   A   S   C   H   P   P   E   A   K   T   W   A   S   R   P
```

FIGURE 1A

```
        387          396          405          414          423          432
CAA GTC CCG GAG CCA AGG CCC CAG GCC CCG GAC CTC TAT GAT GAT GAC CTG GAG
 Q   V   P   E   P   R   P   Q   A   P   D   L   Y   D   D   D   L   E 441          450          459          468          477          486
TTC AGA CCC CCC TCG CGG CCC CAG TCC TCT GAC AAC CAG CAG TAC TTC TGT GCC
 F   R   P   P   S   R   P   Q   S   S   D   N   Q   Q   Y   F   C   A 495          504          513          522          531          540
CCA GCC CCT CTC AGC CCA TCT GCC AGG CCC CGC AGC CCA TGG GGC AAG CTT GAT
 P   A   P   L   S   P   S   A   R   P   R   S   P   W   G   K   L   D 549          558          567          576          585          594
CCC TAT GAT TCC TCT GAG GAT GAC AAG GAG TAT GTG GGC TTT GCA ACC CTC CCC
 P   Y   D   S   S   E   D   D   K   E   Y   V   G   F   A   T   L   P 603          612          621          630          639          648
AAC CAA GTC CAC CGA AAG TCC GTG AAG AAA GGC TTT GAC TTT ACC CTC ATG GTG
 N   Q   V   H   R   K   S   V   K   K   G   F   D   F   T   L   M   V 657          666          675          684          693          702
GCA GGA GAG TCT GGC CTG GGC AAA TCC ACA CTT GTC AAT AGC CTC TTC CTC TCT
 A   G   E   S   G   L   G   K   S   T   L   V   N   S   L   F   L   S 711          720          729          738          747          756
GAT CTG TAC CGG GAC CGG AAA CTT CTT GGT GCT GAA GAG AGG ATC ATG CAA ACT
 D   L   Y   R   D   R   K   L   L   G   A   E   E   R   I   M   Q   T
```

FIGURE 1B

```
      765         774         783         792         801         810
GTG GAG ATC ACT AAG CAT GCA GTG GAC ATA GAA GAG AAG GGT GTG AGG CTG CGG
 V   E   I   T   K   H   A   V   D   I   E   E   K   G   V   R   L   R 819         828         837         846         855         864
CTC ACC ATT GTG GAC ACA CCA GGT TTT GGG GAT GCA GTC AAC ACA GAG TGC
 L   T   I   V   D   T   P   G   F   G   D   A   V   N   T   E   C 873         882         891         900         909         918
TGG AAG CCT GTG GCA GAA TAC ATT GAT CAG CAG TTT GAG CAG TAT TTC CGA GAC
 W   K   P   V   A   E   Y   I   D   Q   Q   F   E   Q   Y   F   R   D 927         936         945         954         963         972
GAG AGT GGC CTG AAC CGA AAG AAC ATC CAA GAC AAC AGG GTG CAC TGC TGC CTG
 E   S   G   L   N   R   K   N   I   Q   D   N   R   V   H   C   C   L 981         990         999        1008        1017        1026
TAC TTC ATC TCA CCC TTC GGC CAT GGG CTC CGG CCA TTG GAT GTT GAA TTC ATG
 Y   F   I   S   P   F   G   H   G   L   R   P   L   D   V   E   F   M 1035        1044        1053        1062        1071        1080
AAG GCC CTG CAT CAG CGG GTC AAC ATC GTG CCT ATC CTG GCT AAG GCA GAC ACA
 K   A   L   H   Q   R   V   N   I   V   P   I   L   A   K   A   D   T 1089        1098        1107        1116        1125        1134
CTG ACA CCT CCC GAA GTG GAC CAC AAA CGC AAG AAA ATC CGG GAG GAG ATT GAG
 L   T   P   P   E   V   D   H   K   R   K   K   I   R   E   E   I   E
```

FIGURE 1C

```
          1143           1152           1161           1170           1179           1188
CAT TTT GGA ATC AAG ATC TAT CAA TTC CCA GAC TGT GAC TCT GAT GAG GAT GAG
 H   F   G   I   K   I   Y   Q   F   P   D   C   D   S   D   E   D   E 1197           1206           1215           1224           1233           1242
GAC TTC AAA TTG CAG GAC CAA GCC CTA AAG GAA AGC ATC CCA TTT GCA GTA ATT
 D   F   K   L   Q   D   Q   A   L   K   E   S   I   P   F   A   V   I 1251           1260           1269           1278           1287           1296
GGC AGC AAC ACT GTA GAG GCC AGA GGG CGG GTT CGA GGT CGA CTC TAC
 G   S   N   T   V   E   A   R   G   R   V   R   G   R   L   Y 1305           1314           1323           1332           1341           1350
CCC TGG GGC ATC GTG GAA GTG AAC CCA GGG CAC TGC GAC TTT GTG AAG CTG
 P   W   G   I   V   E   V   N   P   G   H   C   D   F   V   K   L 1359           1368           1377           1386           1395           1404
AGG ACA ATG CTG GTA CGT ACC CAC ATG CAG GAC CTG AAG GAT GTG ACA CGG GAG
 R   T   M   L   V   R   T   H   M   Q   D   L   K   D   V   T   R   E 1413           1422           1431           1440           1449           1458
ACA CAT TAT GAG AAC TAC CGG GCA CAG TGC ATC CAG AGC ATG ACC CGC CTG GTG
 T   H   Y   E   N   Y   R   A   Q   C   I   Q   S   M   T   R   L   V 1467           1476           1485           1494           1503           1512
GTG AAG GAA CGG AAT CGC AAC AAA CTG ACT CGG GAA AGT GGT ACC GAC TTC CCC
 V   K   E   R   N   R   N   K   L   T   R   E   S   G   T   D   F   P
```

FIGURE 1D

```
                                    1521               1530               1539               1548               1557               1566
                                    ATC CCT GCT GTC CCA CCA GGG ACA GAT CCA GAA ACT GAG AAG CTT ATC CGA GAG
                                     I   P   A   V   P   P   G   T   D   P   E   T   E   K   L   I   R   E 1575               1584               1593               1602               1611               1620
                                    AAA GAT GAG GAG CTG CGG CGG ATG CAG GAG ATG CTA CAC AAA ATA CAA AAA CAG
                                     K   D   E   E   L   R   R   M   Q   E   M   L   H   K   I   Q   K   Q 1629               1638               1647               1656               1665               1674
                                    ATG AAG GAG AAC TAT TAA CTG GCT TTC AGC CCT GGA TAT TTA AAT CTC CTC CTC
                                     M   K   E   N   Y 1683               1692               1701               1710               1719               1728
                                    TTC TTC CTG TCC ATG CCG GCC CCT CCC AGC ACC AGC TCT GCT CAG GCC CCT TCA 1737               1746               1755               1764               1773               1782
                                    GCT ACT GCC ACT TCG CCT TAC ATC CCT GCT GAC TGC CCA GAG ACT CAG AGG AAA 1791               1800               1809               1818
                                    TAA AGT TTA ATA AAT CTG TAG GTG GCA AAA AAA AAA  3'
```

```
                  9              18             27          36          45          54
5' NGA GGC GCG AGG GAG GCG AGC CCG AGC ACT AGC AGC CGG AGT CGG 63             72             81          90          99         108
CGG AAA GCA CCC GGG CGC ACG GNA GAC GGT GCC GCA GCT GCG ATG GCC GTG GCC
                                                          M   A   V   A 117            126            135        144         153         162
GTG GGG AGA CCG TCT AAT GAA GAG CTT CGA AAC TTG TCT TTG TCT GGC CAT GTG
 V   G   R   P   S   N   E   E   L   R   N   L   S   L   S   G   H   V 171            180            189        198         207         216
GGA TTT GAC AGC CTC CCT GAC CAG GTC AAC CTG GTC AAG TCT ACT CAA GGA TTC
 G   F   D   S   L   P   D   Q   V   N   L   V   K   S   T   Q   G   F 225            234            243        252         261         270
TGT TTC AAC ATC CTT TGT GTT GGT GAG ACA GGC ATT GGC AAA TCC ACG TTA ATG
 C   F   N   I   L   C   V   G   E   T   G   I   G   K   S   T   L   M 279            288            297        306         315         324
GAC ACT TTG TTC AAC ACC AAA TTT GAA AGT GAC CCA GCT ACT CAC AAT GAA CCA
 D   T   L   F   N   T   K   F   E   S   D   P   A   T   H   N   E   P 333            342            351        360         369         378
GGT GTT CGG TTA AAA GCC AGA AGT TAT GAG CTT CAG GAA AGC AAT GTA CGG CTG
 G   V   R   L   K   A   R   S   Y   E   L   Q   E   S   N   V   R   L

FIGURE 4A
```

```
        387       396       405       414       423       432
AAG TTA ACC ATT GTT GAC ACC GTG GGA TTT GAC CAG ATA AAT AAA GAT GAC
 K   L   T   I   V   D   T   V   G   F   D   Q   I   N   K   D   D 441       450       459       468       477       486
AGC TAT AAG CCG ATA GTA GAA TAT ATT GAT GCC CAG TTC GAG GCC TAC CTG CAA
 S   Y   K   P   I   V   E   Y   I   D   A   Q   F   E   A   Y   L   Q 495       504       513       522       531       540
GAG GAA TTG AAG ATT AAA CGT TCT CTC TTC AAC TAC CAT GAC ACG AGG ATC CAT
 E   E   L   K   I   K   R   S   L   F   N   Y   H   D   T   R   I   H 549       558       567       576       585       594
GCC TGC CTC TAC TTT ATT GCC CCT ACT GGA CAT TCA CTA AAG TCC CTG GAT CTG
 A   C   L   Y   F   I   A   P   T   G   H   S   L   K   S   L   D   L 603       612       621       630       639       648
GTC ACC ATG AAA AAG CTG GAC AGT AAG AAT GAA CTG CAC AAA ATC ATT CCA ATA ATT GCA AAA
 V   T   M   K   K   L   D   S   K   N   E   L   H   K   I   I   P   I   I   A   K 657       666       675       684       693       702
GCT GAC ACC ATT GCC AAG AAT ATT GCC AAG CTG CAC AAA TTC AAG AGT ATC ATG AGT
 A   D   T   I   A   K   N   E   L   H   K   F   K   S   I   M   S 711       720       729       738       747       756
GAA CTG GTC AGC AAT GGG GTC CAG ATA TAT CAG TTT CCC ACT GAT GAA GAA ACG
 E   L   V   S   N   G   V   Q   I   Y   Q   F   P   T   D   E   E   T
```

FIGURE 4B

```
    765          774          783          792          801          810
GTG GCA GAG ATT AAC GCA ACA ATG AGT GTC CAT CTC CCA TTT GCA GTG GTT GGC
 V   A   E   I   N   A   T   M   S   V   H   L   P   F   A   V   V   G 819          828          837          846          855          864
AGC ACC GAA GAG GTG AAG ATT GGC AAC AAG ATG GCA AAG GCC AGG CAG TAC CCC
 S   T   E   E   V   K   I   G   N   K   M   A   K   A   R   Q   Y   P 873          882          891          900          909          918
TGG GGT GTG GTG CAG GTT GAG AAT CAT TGC GAT TTT GTG AAA CTT CGA
 W   G   V   V   Q   V   E   N   H   C   D   F   V   K   L   R 927          936          945          954          963          972
GAG ATG CTG ATC CGC GTG AAC ATG GAG GAC TTG CGA GAG CAG ACT CAC ACC CGC
 E   M   L   I   R   V   N   M   E   D   L   R   E   Q   T   H   T   R 981          990          999         1008         1017         1026
CAC TAT GAA TTG TAC CGA TGT CGT AAG CTT GAA GAG ATG GGG TTC AAG GAC ACT
 H   Y   E   L   Y   R   C   R   K   L   E   E   M   G   F   K   D   T 1035         1044         1053         1062         1071         1080
GAC CCT GAC AGC AAA CCC TTC AGT CTT CAG GAG ACA TAT GAA GCA AAA AGG AAT
 D   P   D   S   K   P   F   S   L   Q   E   T   Y   E   A   K   R   N 1089         1098         1107         1116         1125         1134
GAA TTC CTG GGA GAA CTG CAG AAG AAA GAA GAA ATG AGA CAA ATG TTT GTT
 E   F   L   G   E   L   Q   K   K   E   E   M   R   Q   M   F   V
```

FIGURE 4C

```
1143                1152            1161             1170           1179            1188
ATG AGA GTG AAG GAG AAA GAA GCT GAA CTT AAG GAG GCA GAG AAA GAG CTT CAC
 M   R   V   K   E   K   E   A   E   L   K   E   A   E   K   E   L   H 1197             1206            1215            1224            1233           1242
GAG AAG TTT GAC CTT CTA AAG CGG ACA CAC CAA GAA AAG AAA GTG GAA
 E   K   F   D   L   L   K   R   T   H   Q   E   E   K   K   V   E 1251             1260            1269            1278            1287            1296
GAC AAG AAG GAG CTT GAG GAG GTG GAG AAC TTC CAG AAG AAA GCA
 D   K   K   K   E   L   E   E   V   E   N   F   Q   K   K   A 1305             1314            1323            1332            1341           1350
GCG GCT CAG TTA CTA CAG TCC CAG GCC CAG CAA TCT GGG GCC CAA ACC AAG
 A   A   Q   L   L   Q   S   Q   A   Q   Q   S   G   A   Q   T   K 1359             1368            1377            1386            1395            1404
AAA GAC AAG GAT AAG AAA AAC TGA CCA TCT GCC TCT TGA GAG AGA GAG AAG TGG
 K   D   K   D   K   K   N 1413             1422            1431            1440            1449           1458
GCA TCC TTC CTT TAA ATT CAG GAA CCA CTG TTG TTT TAT TTG ACT TTT TCT GTT 1467             1476            1485            1494            1503            1512
ACT TGC ATC CCT TAT ATA AGT TGT TTT GGA TTT GGG ACT ATG TTT TGG GGG AGA
```

FIGURE 4D

```
     1521        1530        1539        1548        1557     1566
AAA ACT CCA GTT AGT TCT GTT TTT TGT ATT GGT TAT TCA GCT TAC TTT TGG TAT 1575        1584        1593        1602        1611     1620
CAA AAT TAT GCC AGT TTT AAG CTC ACT TGA GTG AAG TTT AAG TCA CAA GAT TCT 1629        1638        1647        1656        1665     1674
GTT TAA CAT GCT TTC CTT GTT TTG GAA ACA ACC AAA AAC TTC CCT TTT TTG TTA 1683        1692        1701        1710        1719     1728
CGG GAT TTT GAC CTA CAA ATC CTA ATC ATG TTT AAA ATG TGC CGG TGT TGG GTA 1737        1746        1755        1764        1773     1782
GAT GAC TTT TCT GCC TCT GGG GTT CAA TTT ATA TTT AAA GAT ACC TTA AAA TAA

1791
AAA AAA AAG AAA A 3'
```

FIGURE 4E

```
  1  MAVAVGRPSNEELRNLSLSGHVGFDSLPDQLVNKSTSQGF  348429
  1  --TDIARQVGEGCRTVPLAGHVGFDSLPDQLVNKSVSQGF  GI 1469179

41  CFNILCVGETGIGKSTLMDTLFNTKFESDPATHNEPGVRL  348429
 39  CFNILCVGETGLGKSTLMDTLFNTKFEGEPATHTQPGVQL  GI 1469179

81  KARSYELQESNVRLKLTIVDTVGFGDQINKDDSYKPIVEY  348429
 79  QSNTYDLQESNVRLKLTIVSTVGFGDQINKEDSYKPIVEF  GI 1469179

121  IDAQFEAYLQEELKIKRSLFNYHDTRIHACLYFIAPTGHS  348429
119  IDAQFEAYLQEELKIRRVLHTYHDSRIHVCLYFIAPTGHS  GI 1469179

161  LKSLDLVTMKKLDSKVNIIPIIAKADTIAKNELHKFKSKI  348429
159  LKSLDLVTMKKLDSKVNIIPIIAKADAISKSELTKFKIKI  GI 1469179

201  MSELVSNGVQIYQFPTDEETVAEINATMSVHLPFAVVGST  348429
199  TSELVSNGVQIYQFPTDDESVAEINGTMNAHLPFAVIGST  GI 1469179

241  EEVKIGNKMAKARQYPWGVVQVENENHCDFVKLREMLIRV  348429
239  ELKIGNKMMRARQYPWGTVQVENEAHCDFVKLREMLIRV  GI 1469179
```

FIGURE 5A

```
281 NMEDLREQTHTRHYELYRRCKLEEMGFKDTDPDSKPFSLQ    348429
279 NMEDLREQTHTRHYELYRRCKLEEMGFKDTDPDSKPFSLQ    GI 1469179

321 ETYEAKRNEFLGELQKKEEEMRQMFVMRVKEKEAELKEAE    348429
319 ETYEAKRNEFLGELQKKEEEMRQMFVQRVKEKEAELKEAE    GI 1469179

361 KELHEKFDLLKRTHQEEKKVEDKKKELEEEVNNFQKKKA     348429
359 KELHEKFDRLKKLHQDEKKKLEDKKKSLDDEVNAFKQRKT    GI 1469179

401 AAQLLQSQAQQSGAQQT-KKDKDKN                   348429
399 AAELLQSQGSQAGGSQTLKRDKEKKN                  GI 1469179
```

FIGURE 5B

```
                    9              18          27          36          45          54
5' NNT GCG CCT CAG CCC GCG CGC TCG CAG CTT CTC GCT CTC GCC TGC CTG CCC GCT 63             72          81          90          99         108
   CCC TTG CTT GCT CGC GCT TTC GCT CGC CCT CTC GAG GAT CGA GGG GAC TCT 117            126         135         144         153         162
   GAC CAC AGC CTG TGG CTG GGA AGG GAG ACA GAG GCG GCG GCT CAG GGG AAA 171            180         189         198         207         216
   CGA GGC TGC AGT GGT AGT AGG AAG ATG TCG GGC GAG GAC GAA CAG GAG
                                         M   S   G   E   D   E   Q   E 225            234         243         252         261         270
   CAA ACT ATC GCT GAG GAC CTG GTC ACC AAG TAT AAG ATG GGG GGC GAC ATC
    Q   T   I   A   E   D   L   V   T   K   Y   K   M   G   G   D   I 279            288         297         306         315         324
   GCC AAC AGG GTA CTT CGG TCC TTG GTG GAA GCA TCT AGC TCA GGT GTG TCG GTA
    A   N   R   V   L   R   S   L   V   E   A   S   S   S   G   V   S   V 333            342         351         360         369         378
   TTG AGC CTG TGT GAG AAA GGT GAT GCC ATG ATT ATG GAA GAA ACA GGG AAA ATC
    L   S   L   C   E   K   G   D   A   M   I   M   E   E   T   G   K   I
```

FIGURE 7A

```
      387         396         405         414         423         432
TTC AAG AAA GAA AAG GAA ATG AAG AAA GGT ATT GCT TTT CCC ACC AGC ATT TCG
 F   K   K   E   K   E   M   K   K   G   I   A   F   P   T   S   I   S 441         450         459         468         477         486
GTA AAT AAC TGT GTA TGT CAC TTC TCC CCT TTG AAG AGC GAC CAG GAT TAT ATT
 V   N   N   C   V   C   H   F   S   P   L   K   S   D   Q   D   Y   I 495         504         513         522         531         540
CTC AAG GAA GGT GAC TTG GTA AAA ATT GAC CTT GGG GTC CAT GTG GAT GGC TTC
 L   K   E   G   D   L   V   K   I   D   L   G   V   H   V   D   G   F 549         558         567         576         585         594
ATC GCT AAT GTA GCT CAC ACT TTT GTG GTT GAT GTA GCT CAG GGG ACC CAA GTA
 I   A   N   V   A   H   T   F   V   V   D   V   A   Q   G   T   Q   V 603         612         621         630         639         648
ACA GGG AGG AAA GCA GAT GTT ATT AAG GCA GCT CAC CTT TGT GCT GAA GCT GCC
 T   G   R   K   A   D   V   I   K   A   A   H   L   C   A   E   A   A 657         666         675         684         693         702
CTA CGC CTG GTC AAA CCT GGA AAT CAG AAC ACA CAA GTG ACA GAA GCC TGG AAC
 L   R   L   V   K   P   G   N   Q   N   T   Q   V   T   E   A   W   N 711         720         729         738         747         756
AAA GTT GCC CAC TCA TTT AAC TGC ACG CCA ATA GAA GGT ATG CTG TCA CAC CAG
 K   V   A   H   S   F   N   C   T   P   I   E   G   M   L   S   H   Q
```

FIGURE 7B

```
       765             774             783             792             801             810.
TTG AAG CAG CAT GTC ATC GAT GGA GAA AAA ACC ATT ATC CAG AAT CCC ACA GAC
 L   K   Q   H   V   I   D   G   E   K   T   I   I   Q   N   P   T   D 819             828             837             846             855             864
CAG CAG AAG AAG GAC CAT GAA AAA GCT GAA TTT GAG GTA CAT GAA GTA TAT GCT
 Q   Q   K   K   D   H   E   K   A   E   F   E   V   H   E   V   Y   A 873             882             891             900             909             918
GTG GAT GTT CTC GTC AGC TCA GGA GAG GGC AAG GAT GCC AAG GAT GCA GGA CAG AGA
 V   D   V   L   V   S   S   G   E   G   K   D   A   K   D   A   G   Q   R 927             936             945             954             963             972
ACC ACT ATT TAC AAA CGA GAC CCC TCT AAA CAG TAT GGA CTG AAA ATG AAA ACT
 T   T   I   Y   K   R   D   P   S   K   Q   Y   G   L   K   M   K   T 981             990             999            1008            1017            1026
TCA CGT GCC TTC TTC TTC AGT GAG GTG GAA AGG CGT TTT GAT GCC ATG CCG TTT ACT
 S   R   A   F   F   F   S   E   V   E   R   R   F   D   A   M   P   F   T 1035            1044            1053            1062            1071            1080
TTA AGA GCA TTT GAA GAT GAG AAG AAG GCT CGG ATG GGT GTG GAG TGC GCC
 L   R   A   F   E   D   E   K   K   A   R   M   G   V   E   C   A 1089            1098            1107            1116            1125            1134
AAA CAT GAA CTG CTG CAA CCA TTT AAT GTT CTC TAT GAG AAG GAG GGT GAA TTT
 K   H   E   L   L   Q   P   F   N   V   L   Y   E   K   E   G   E   F
```

FIGURE 7C

```
           1143            1152                1161              1170              1179.             1188
     GTT GCC CAG TTT AAA TTT ACA GTT CTG CTC ATG CCC AAT GGC CCC ATG CGG ATA
      V   A   Q   F   K   F   T   V   L   L   M   P   N   G   P   M   R   I 1197            1206              1215              1224              1233              1242
     ACC AGT GGT CCC TTC GAG CCT GAC CTC TAC AAG TCT GAG ATG GAG GTC CAG GAT
      T   S   G   P   F   E   P   D   L   Y   K   S   E   M   E   V   Q   D 1251            1260              1269              1278              1287              1296
     GCA GAG CTA AAG GCC CTC CTC CAG AGT TCT GCA AGT CGA AAA ACC CAG AAA AAG
      A   E   L   K   A   L   L   Q   S   S   A   S   R   K   T   Q   K   K 1305            1314              1323              1332              1341              1350
     AAA AAA AAG GCC TCC AAG ACT GCA GAG AAT GCC ACC AGT GGG GAA ACA TTA
      K   K   K   A   S   K   T   A   E   N   A   T   S   G   E   T   L 1359            1368              1377              1386              1395              1404
     GAA GAA AAT GAA GCT GGG GAC TGA GGT GGG TCC CAT CTC CCC AGC TTG CTG CTC
      E   E   N   E   A   G   D 1413            1422              1431              1440              1449              1458
     CTG CCT CAT CCC CTT CCC ACC ATA CCC CAG ACT CTG TGA AGG CAG TTT TTC TCC  3'
```

CELL DIVISION REGULATORS

FIELD OF THE INVENTION

This invention relates to nucleic acid and amino acid sequences of three new human cell division regulators and to the use of these sequences in the diagnosis, prevention, and treatment of inflammation and disorders associated with cell proliferation and apoptosis.

BACKGROUND OF THE INVENTION

Cell division is the fundamental process by which living organisms grow and reproduce. The cycle of cell division consists of three principle events: interphase, mitosis, and cytokinesis. During interphase, replication of the DNA and production of essential proteins are synthesized. In mitosis, the nuclear material is divided and separated to opposite halves of the cell. In cytokinesis, the cell cytoplasm is divided. These cell cycle events are regulated by various cell division regulators.

A group of cell division regulatory proteins active in the interphase is related to nuclear redistribution and modulation. These regulatory proteins include the proliferating cell nuclear antigen (PCNA) which is identified as the DNA polymerase-δ auxiliary protein (Prelich, G. et al. (1987) Nature 326: 517–520), the *Schizosaccharomyces pombe* Cdc21p gene (Coxon, A. et al. (1992) Nucleic Acids Res. 20: 5571–5577), and a murine cell cycle-specifically modulated nuclear protein, p38-2G4 (Radomski, N. and Jost, E. (1995) Exp. Cell Res. 220: 434–445). p38-2G4 is a nuclear protein of 38 kDa and is a murine homolog of *S. pombe* Cdc21p gene product. p38-2G4 shows its highest expression between the G1 phase and the mid S phase and contains a number of putative phosphorylation sites, a cryptic nuclear localization signal, and an amphipathic helical domain.

The process of cytokinesis and septum formation has been well studied. Cytokinesis is believed to be mediated by the filaments and other components formed from GTP-binding proteins (Mori, et al. (1996) Cytogenet. Cell Genet. 73: 224–227). Septins are a family of proteins that are involved in septum formation. (Longtine, M. S. et al. (1996) Curr. Opin. Cell Biol. 8:106–119). In yeast, four gene products (CDC3, CDC10, CDC11, and CDC12) are members of this family and are associated with the "bud filament" which is located directly inside the cytoplasmic membrane. Mutations in any of the CDC genes disrupts cytokinesis and gives rise to multi-nucleated cells with abnormal bud growth.

Homologs of the yeast septins have been found in *Drosophila melanogaster* (Sep2), mouse (H5; proliferation associated protein 1; Nakagawa, Y. et al. (1996) unpublished), and human (KIAA0128; cell division control related protein; Zieger, B. et al. (1997) J. Clin. Invest. 99: 520–525; Nagase, T. et al. (1996) DNA Res. 3: 321–329). Most of these proteins share three domains rich in basic amino acids that are a common motif of GTP-binding proteins and of the GTPase superfamily. The first of these three domains, the sequence GXXGXGKST, is thought to be an ATP/GTP-binding site (P-loop) that may be involved in septin assembly or function (Saraste, M. et al. (1990) Trends Biochem. Sci. 15:430–34). Most of the known septins also contain predicted coiled-coil domains of 35 to 98 amino acids near the C-termini (Longtine et al., supra). These domains may be involved in homotypic or heterotypic interactions among the septins themselves and/or with other proteins.

The discovery of three new human cell division regulators and the polynucleotides encoding them satisfies a need in the art by providing new compositions which are useful in the diagnosis, prevention, and treatment of inflammation and disorders associated with cell proliferation and apoptosis.

SUMMARY OF THE INVENTION

The invention features three substantially purified polypeptides, designated individually as HCDR-1, HCDR-2, and HCDR-3, and collectively as HCDR, having the amino acid sequences shown in SEQ ID NO:1, SEQ ID NO:3, and SEQ ID NO:5.

The invention further provides an isolated and substantially purified polynucleotide sequence encoding the polypeptide HCDR-1, comprising the amino acid sequence of SEQ ID NO:1 or fragments thereof and compositions comprising said polynucleotide sequence. The invention also provides a polynucleotide sequence which hybridizes under stringent conditions to the polynucleotide sequence encoding the amino acid sequence SEQ ID NO:1 or fragments of said polynucleotide sequence. The invention further provides a polynucleotide sequence comprising the complement of the polynucleotide sequence encoding the amino acid sequence of SEQ ID NO:1, or fragments or variants of said polynucleotide sequence.

The invention also provides an isolated and purified sequence comprising SEQ ID NO:2, or variants thereof. In addition, the invention provides a polynucleotide sequence which hybridizes under stringent conditions to the polynucleotide sequence of SEQ ID NO:2. The invention also provides a polynucleotide sequence comprising the complement of SEQ ID NO:2, or fragments or variants thereof.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:1, or a fragment thereof, the method comprising the steps of: a) culturing the host cell containing an expression vector containing at least a fragment of the polynucleotide sequence encoding HCDR-1 under conditions suitable for the expression of the polypeptide; and b) recovering the polypeptide from the host cell culture.

The invention also provides a pharmaceutical composition comprising a substantially purified HCDR-1 having the amino acid sequence of SEQ ID NO:1 in conjunction with a suitable pharmaceutical carrier.

The invention also provides a purified antagonist of the polypeptide of SEQ ID NO:1. In one aspect the invention provides a purified antibody which binds to a polypeptide comprising the amino acid sequence of SEQ ID NO:1.

Still further, the invention provides a purified agonist of the polypeptide of SEQ ID NO:1.

The invention also provides a method for stimulating cell proliferation comprising administering to a cell an effective amount of purified HCDR-1.

The invention also provides a method for preventing or treating a disorder associated with an increase in apoptosis comprising administering to a subject in need of such treatment an effective amount of a pharmaceutical composition comprising purified HCDR-1.

The invention also provides a method for preventing or treating a cancer comprising administering to a subject in need of such treatment an effective amount of an antagonist of HCDR-1.

The invention also provides a method for preventing or treating an inflammation comprising administering to a subject in need of such treatment an effective amount of an antagonist of HCDR-1.

The invention also provides a method for detecting a polynucleotide which encodes HCDR-1 in a biological sample comprising the steps of: a) hybridizing the complement of the polynucleotide sequence which encodes SEQ ID NO:1 to nucleic acid material of a biological sample, thereby forming a hybridization complex; and b) detecting the hybridization complex, wherein the presence of the complex correlates with the presence of a polynucleotide encoding HCDR-1 in the biological sample. In one aspect the nucleic acid material of the biological sample is amplified by the polymerase chain reaction prior to hybridization.

Still further, the invention provides an isolated and substantially purified polynucleotide sequence encoding the polypeptide HCDR-2, comprising the amino acid sequence of SEQ ID NO:3 or fragments thereof and compositions comprising said polynucleotide sequence. The invention also provides a polynucleotide sequence which hybridizes under stringent conditions to the polynucleotide sequence encoding the amino acid sequence SEQ ID NO:3 or fragments of said polynucleotide sequence. The invention further provides a polynucleotide sequence comprising the complement of the polynucleotide sequence encoding the amino acid sequence of SEQ ID NO:3, or fragments or variants of said polynucleotide sequence.

The invention also provides an isolated and purified sequence comprising SEQ ID NO:4, or variants thereof. In addition, the invention provides a polynucleotide sequence which hybridizes under stringent conditions to the polynucleotide sequence of SEQ ID NO:4. The invention also provides a polynucleotide sequence comprising the complement of SEQ ID NO:4, or fragments or variants thereof.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:3, or a fragment thereof, the method comprising the steps of: a) culturing the host cell containing an expression vector containing at least a fragment of the polynucleotide sequence encoding HCDR-2 under conditions suitable for the expression of the polypeptide; and b) recovering the polypeptide from the host cell culture.

The invention also provides a pharmaceutical composition comprising a substantially purified HCDR-2 having the amino acid sequence of SEQ ID NO:3 in conjunction with a suitable pharmaceutical carrier.

The invention also provides a purified antagonist of the polypeptide of SEQ ID NO:3. In one aspect the invention provides a purified antibody which binds to a polypeptide comprising the amino acid sequence of SEQ ID NO:3.

Still further, the invention provides a purified agonist of the polypeptide of SEQ ID NO:3.

The invention also provides a method for stimulating cell proliferation comprising administering to a cell an effective amount of purified HCDR-2.

The invention also provides a method for preventing or treating a disorder associated with an increase in apoptosis comprising administering to a subject in need of such treatment an effective amount of a pharmaceutical composition comprising purified HCDR-2.

The invention also provides a method for preventing or treating a cancer comprising administering to a subject in need of such treatment an effective amount of an antagonist of HCDR-2.

The invention also provides a method for preventing or treating an inflammation comprising administering to a subject in need of such treatment an effective amount of an antagonist of HCDR-2.

The invention also provides a method for detecting a polynucleotide which encodes HCDR-2 (SEQ ID NO:3) in a biological sample comprising the steps of: a) hybridizing the complement of the polynucleotide sequence which encodes SEQ ID NO:3 to nucleic acid material of a biological sample, thereby forming a hybridization complex; and b) detecting the hybridization complex, wherein the presence of the complex correlates with the presence of a polynucleotide encoding HCDR-2 in the biological sample. In one aspect the nucleic acid material of the biological sample is amplified by the polymerase chain reaction prior to hybridization.

Still further, the invention provides an isolated and substantially purified polynucleotide sequence encoding the polypeptide HCDR-3, comprising the amino acid sequence of SEQ ID NO:5 or fragments thereof and compositions comprising said polynucleotide sequence. The invention also provides a polynucleotide sequence which hybridizes under stringent conditions to the polynucleotide sequence encoding the amino acid sequence SEQ ID NO:5 or fragments of said polynucleotide sequence. The invention further provides a polynucleotide sequence comprising the complement of the polynucleotide sequence encoding the amino acid sequence of SEQ ID NO:5, or fragments or variants of said polynucleotide sequence.

The invention also provides an isolated and purified sequence comprising SEQ ID NO:6, or variants thereof. In addition, the invention provides a polynucleotide sequence which hybridizes under stringent conditions to the polynucleotide sequence of SEQ ID NO:6. The invention also provides a polynucleotide sequence comprising the complement of SEQ ID NO:6, or fragments or variants thereof.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:5, or a fragment thereof, the method comprising the steps of: a) culturing the host cell containing an expression vector containing at least a fragment of the polynucleotide sequence encoding HCDR-3 under conditions suitable for the expression of the polypeptide; and b) recovering the polypeptide from the host cell culture.

The invention also provides a pharmaceutical composition comprising a substantially purified HCDR-3 having the amino acid sequence of SEQ ID NO:5 in conjunction with a suitable pharmaceutical carrier.

The invention also provides a purified antagonist of the polypeptide of SEQ ID NO:5. In one aspect the invention provides a purified antibody which binds to a polypeptide comprising the amino acid sequence of SEQ ID NO:5.

Still further, the invention provides a purified agonist of the polypeptide of SEQ ID NO:5.

The invention also provides a method for stimulating cell proliferation comprising administering to a cell an effective amount of purified HCDR-3.

The invention also provides a method for preventing or treating a disorder associated with an increase in apoptosis comprising administering to a subject in need of such treatment an effective amount of a pharmaceutical composition comprising purified HCDR-3.

The invention also provides a method for preventing or treating a cancer comprising administering to a subject in need of such treatment an effective amount of an antagonist of HCDR-3.

The invention also provides a method for preventing or treating an inflammation comprising administering to a subject in need of such treatment an effective amount of an antagonist of HCDR-3.

The invention also provides a method for detecting a polynucleotide which encodes HCDR-3 in a biological sample comprising the steps of: a) hybridizing the complement of the polynucleotide sequence which encodes SEQ ID NO:5 to nucleic acid material of a biological sample, thereby forming a hybridization complex; and b) detecting the hybridization complex, wherein the presence of the complex correlates with the presence of a polynucleotide encoding HCDR-3 in the biological sample. In one aspect the nucleic acid material of the biological sample is amplified by the polymerase chain reaction prior to hybridization.

BRIEF DESCRIPTION OF THE FIGURES

FIGS. 1A, 1B, 1C, 1D, and 1E show the amino acid sequence (SEQ ID NO:1) and nucleic acid sequence (SEQ ID NO:2) of HCDR-1. The alignment was produced using MACDNASIS PRO™ software (Hitachi Software Engineering Co. Ltd. San Bruno, Calif.).

FIGS. 2A and 2B show the amino acid sequence alignments among HCDR-1 (26459; SEQ ID NO:1), a mouse H5 protein (GI 51203; SEQ ID NO:7), and a human cell division control related protein (GI 1809317; SEQ ID NO:8), produced using the multisequence alignment program of DNASTAR™ software (DNASTAR Inc, Madison Wis.).

FIGS. 4A, 4B, 4C, 4D, and 4E show the amino acid sequence (SEQ ID NO:3) and nucleic acid sequence (SEQ ID NO:4) of HCDR-2. The alignment was produced using MACDNASIS PRO™ software (Hitachi Software Engineering Co. Ltd. San Bruno, Calif.).

FIGS. 5A and 5B show the amino acid sequence alignments between HCDR-2 (348429; SEQ ID NO:3) and a human homolog of CDC10, KIAA0128 (GI 1469179; SEQ ID NO:9), produced using the multisequence alignment program of DNASTAR™ software (DNASTAR Inc, Madison Wis.).

FIGS. 7A, 7B, 7C, and 7D show the amino acid sequence (SEQ ID NO:5) and nucleic acid sequence (SEQ ID NO:6) of HCDR-3. The alignment was produced using MACDNASIS PRO™ software (Hitachi Software Engineering Co. Ltd. San Bruno, Calif.).

FIGS. 8A and 8B show the amino acid sequence alignments between HCDR-3 (2458438; SEQ ID NO:5) and a mouse proliferation-associated protein 1 (GI 1167967; SEQ ID NO:10), produced using the multisequence alignment program of DNASTAR™ software (DNASTAR Inc, Madison Wis.).

DESCRIPTION OF THE INVENTION

Figure 3A:
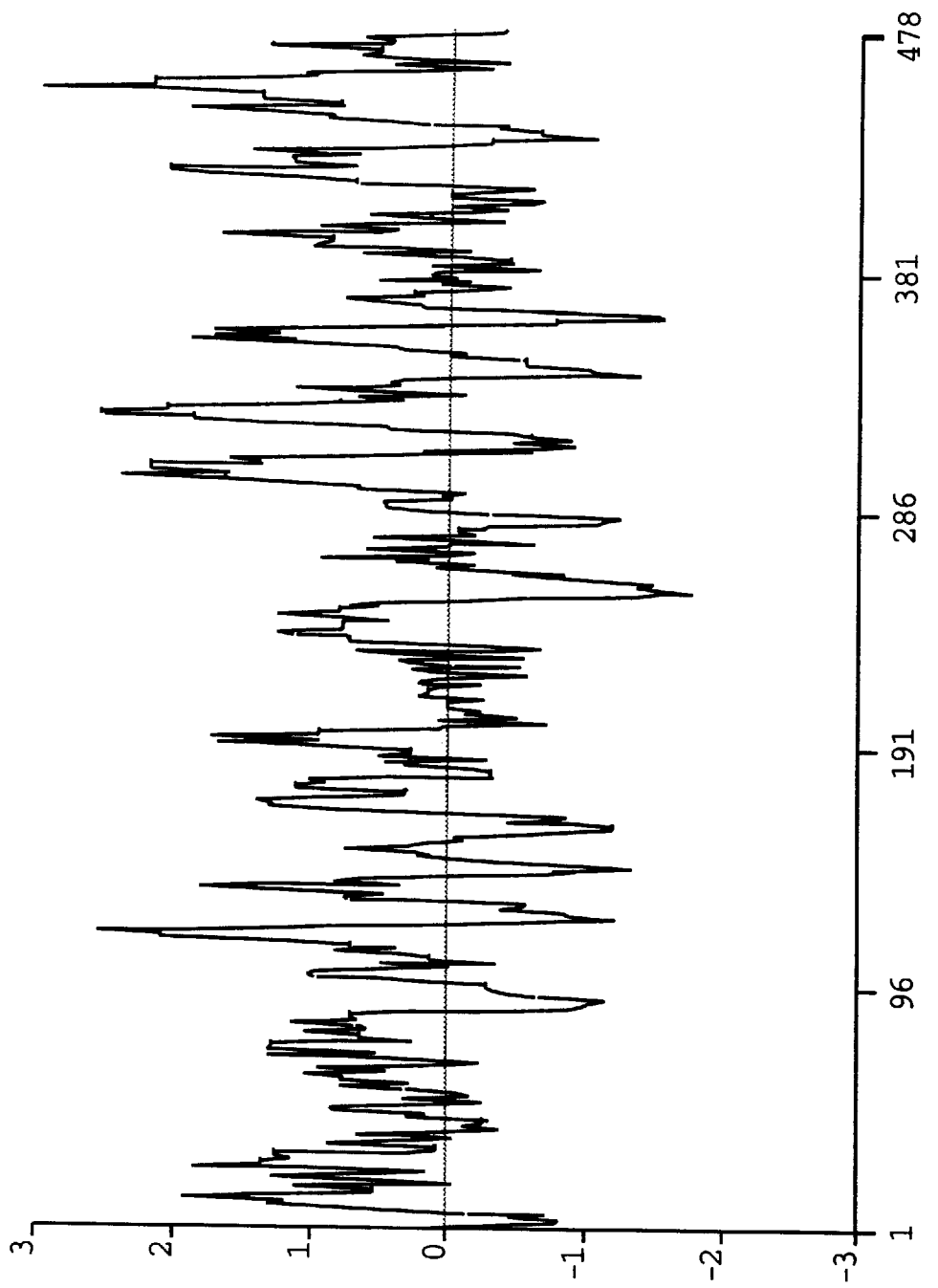
FIGS. 3A and 3B show the hydrophobicity plots for HCDR-1 (SEQ ID NO:1) and the mouse H5 protein (SEQ ID NO:7), respectively. The positive X axis reflects amino acid position, and the negative Y axis, hydrophobicity (MACDNASIS PRO software).

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

Definitions

HCDR, as used herein, refers to the amino acid sequences of substantially purified HCDR obtained from any species, particularly mammalian, including bovine, ovine, porcine, murine, equine, and preferably human, from any source whether natural, synthetic, semi-synthetic, or recombinant.

The term "agonist", as used herein, refers to a molecule which, when bound to HCDR, increases or prolongs the duration of the effect of HCDR. Agonists may include proteins, nucleic acids, carbohydrates, or any other molecules which bind to and modulate the effect of HCDR.

An "allele" or "allelic sequence", as used herein, is an alternative form of the gene encoding HCDR. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding HCDR, as used herein, include those with deletions, insertions, or substitutions of different nucleotides resulting in a polynucleotide that encodes the same or a functionally equivalent HCDR. Included within this definition are polymorphisms which may or may not be readily detectable using a particular oligonucleotide probe of the polynucleotide encoding HCDR, and improper or unexpected hybridization to alleles, with a locus other than the normal chromosomal locus for the polynucleotide sequence encoding HCDR. The encoded protein may also be "altered" and contain deletions, insertions, or substitutions of amino acid residues which produce a silent change and result in a functionally equivalent HCDR. Deliberate amino acid substitutions may be made on the basis of similarity in polarity, charge, solubility, hydrophobicity, hydrophilicity, and/or the amphipathic nature of the residues as long as the biological or immunological activity of HCDR is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence", as used herein, refers to an oligopeptide, peptide, polypeptide, or protein sequence, and fragment thereof, and to naturally occurring or synthetic molecules. Fragments of HCDR are preferably about 5 to about 15 amino acids in length and retain the biological activity or the immunological activity of HCDR. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification", as used herein, refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "antagonist", as used herein, refers to a molecule which, when bound to HCDR, decreases the amount or the duration of the effect of the biological or immunological activity of HCDR. Antagonists may include proteins, nucleic acids, carbohydrates, antibodies or any other molecules which decrease the effect of HCDR.

As used herein, the term "antibody" refers to intact molecules as well as fragments thereof, such as Fa, F(ab')$_2$, and Fv, which are capable of binding the epitopic determinant. Antibodies that bind HCDR polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic HCDR, or any oligopeptide thereof, to induce a specific immune response in appropriate animals or cells and to bind with specific antibodies.

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence", as used herein, refers broadly to any composition containing the given polynucleotide sequence. The composition may comprise a dry formulation or an aqueous solution. Compositions comprising polynucleotide sequences encoding HCDR (SEQ ID NO:1, SEQ ID NO:3, or SEQ ID NO:5) or fragments thereof (e.g., SEQ ID NO:2, SEQ ID NO:4, SEQ ID NO:6 and fragments thereof) may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

"Consensus", as used herein, refers to a nucleic acid sequence which has been resequenced to resolve uncalled bases, has been extended using XL-PCR™ (Perkin Elmer, Norwalk, Conn.) in the 5' and/or the 3' direction and resequenced, or has been assembled from the overlapping sequences of more than one Incyte Clone using a computer program for fragment assembly (e.g., GELVIEW™ Fragment Assembly system, GCG, Madison, Wis.). Some sequences have been both extended and assembled to produce the consensus sequence.

The term "correlates with expression of a polynucleotide", as used herein, indicates that the detection of the presence of ribonucleic acid that is similar to SEQ ID NO:2, SEQ ID NO:4, or SEQ ID NO:6 by northern analysis is indicative of the presence of mRNA encoding HCDR in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to HCDR or the encoded HCDR. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Human artificial chromosomes (HACs) are linear microchromosomes which may contain DNA sequences of 10K to 10M in size and contain all of the elements required for stable mitotic chromosome segregation and maintenance (Harrington, J. J. et al. (1997) Nat Genet. 15:345–355).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Microarray" refers to an array of distinct polynucleotides or oligonucleotides synthesized on a substrate, such as paper, nylon or other type of membrane, filter, chip, glass slide, or any other suitable solid support.

The term "modulate", as used herein, refers to a change in the activity of HCDR. For example, modulation may cause an increase or a decrease in protein activity, binding characteristics, or any other biological, functional or immunological properties of HCDR.

"Nucleic acid sequence" as used herein refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides than in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or a hybridization assay, or a microarray. As used herein, oligonucleotide is substantially equivalent to the terms "amplimers", "primers", "oligomers", and "probes", as commonly defined in the art. "Peptide nucleic acid", PNA as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8:53–63).

The term "portion", as used herein, with regard to a protein (as in "a portion of a given protein") refers to fragments of that protein. The fragments may range in size from five amino acid residues to the entire amino acid sequence minus one amino acid. Thus, for example, a protein "comprising at least a portion of the amino acid sequence of SEQ ID NO:1" encompasses the full-length HCDR-1 and fragments thereof.

The term "sample", as used herein, is used in its broadest sense. A biological sample suspected of containing nucleic acid encoding HCDR, or fragments thereof, or HCDR itself may comprise a bodily fluid, extract from a cell, chromosome, organelle, or membrane isolated from a cell, a cell, genomic DNA, RNA, or cDNA (in solution or bound to a solid support, a tissue, a tissue print, and the like).

The terms "specific binding" or "specifically binding", as used herein, refers to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

The terms "stringent conditions" or "stringency", as used herein, refer to the conditions for hybridization as defined by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. below the melting temperature of the probe to about 20° C. to 25° C. below the melting temperature). One or more factors may be varied to generate conditions of either low or high stringency different from, but equivalent to, the above listed conditions.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of HCDR, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

The Invention

The invention is based on the discovery of three new human cell division regulators (hereinafter collectively referred to as "HCDR"), the polynucleotides encoding HCDR, and the use of these compositions for the diagnosis, prevention, or treatment of inflammation and disorders associated with cell proliferation and apoptosis.

Nucleic acids encoding the HCDR-1 of the present invention were first identified in Incyte Clone 26459 from a fetal spleen tissue cDNA library (SPLNFET01) using a computer search for amino acid sequence alignments. A consensus sequence, SEQ ID NO:2, was derived from the following overlapping and/or extended nucleic acid sequences: Incyte Clones 26459 (SPLNFET01), 100469 (ADRENOT01), and 240018 (HIPONOT01).

Figure 2A:
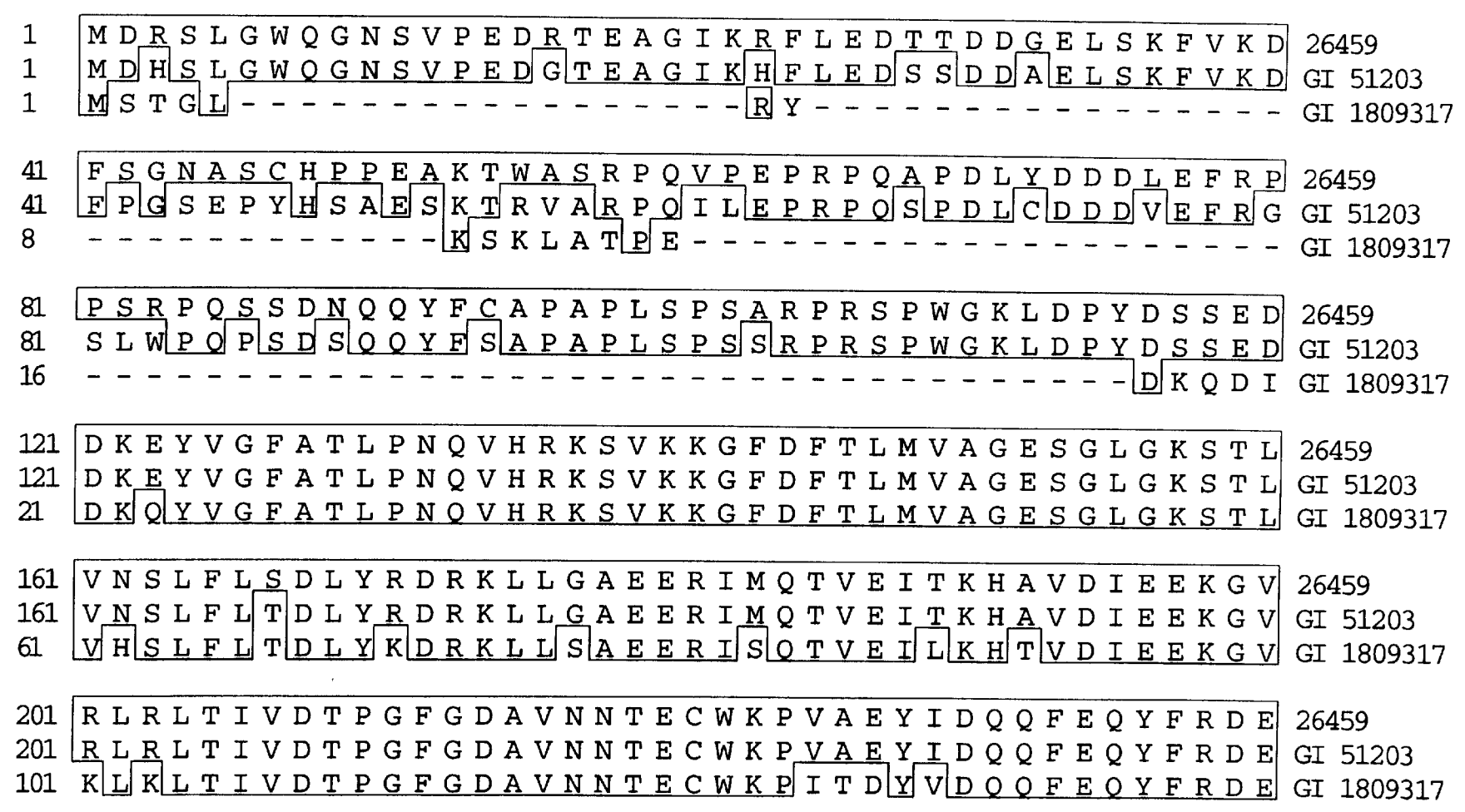
Figure 2B:
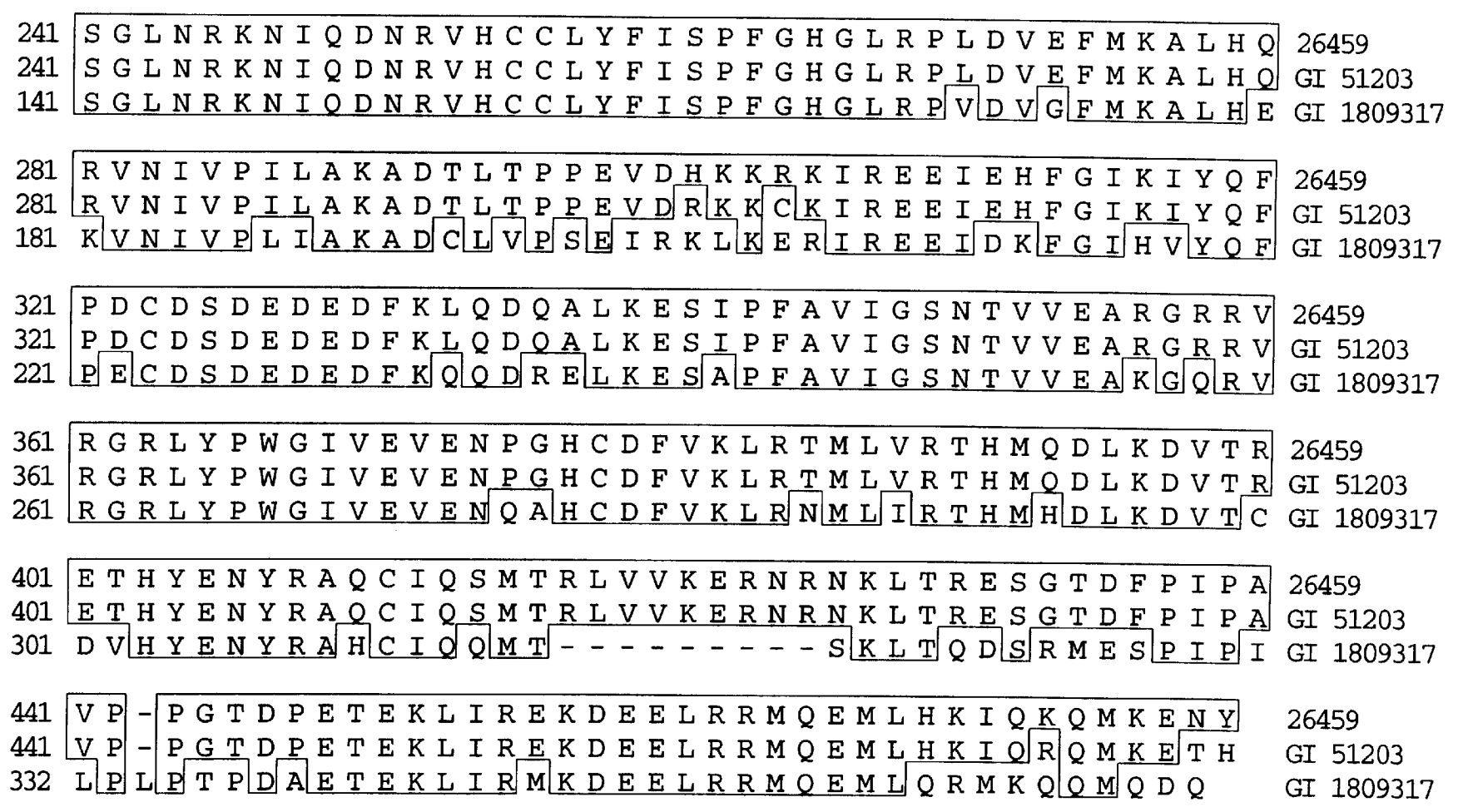
Figure 3B:
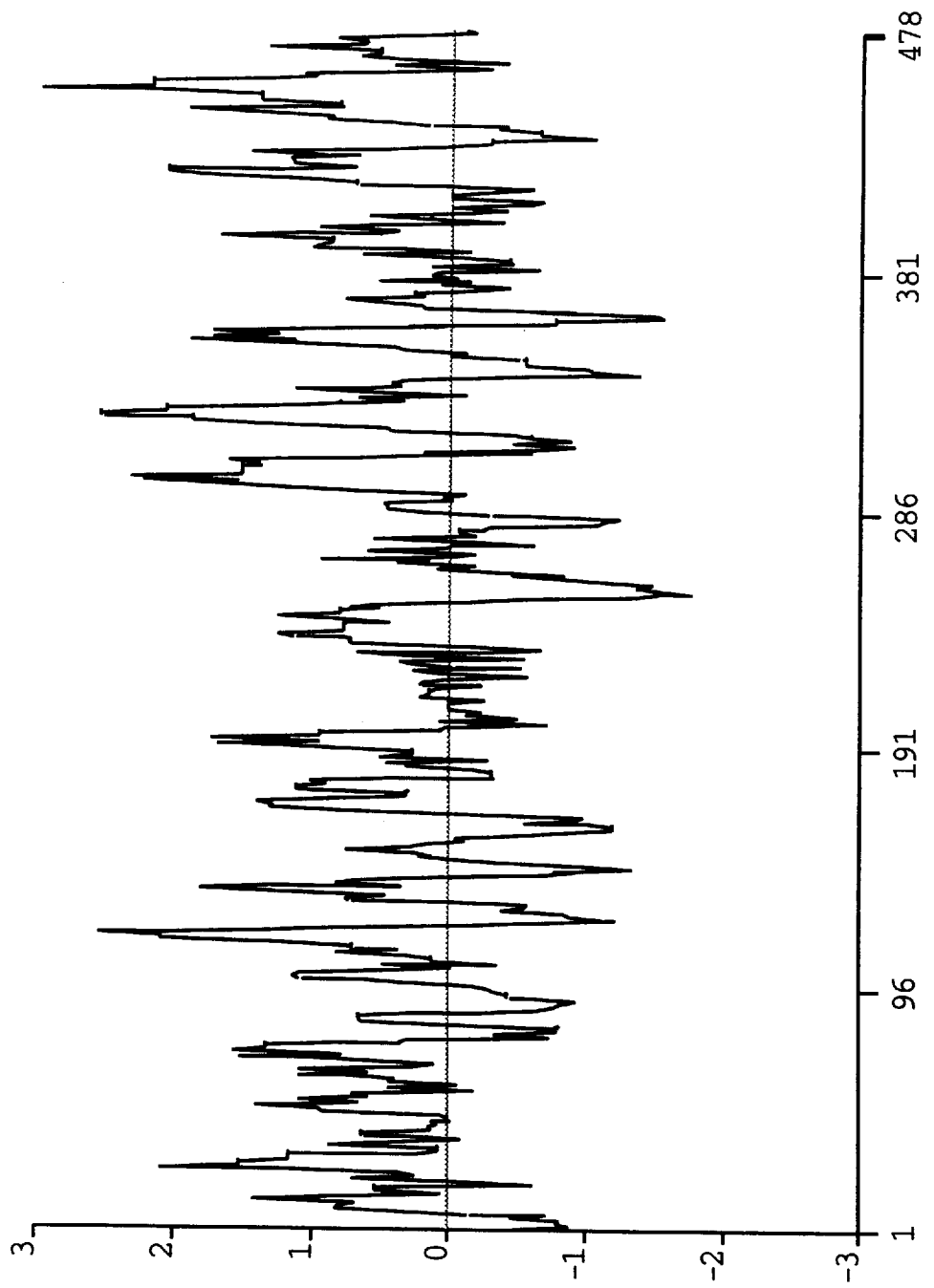

In one embodiment, the invention encompasses a polypeptide, HCDR-1, comprising the amino acid sequence of SEQ ID NO:1, as shown in FIGS. 1A, 1B, 1C, 1D, and 1E. HCDR-1 is 478 amino acids in length. It has a conserved ATP/GTP-binding site encompassing residues G151–S158, analogous to other identified septins. HCDR-1 has one potential amidation site encompassing residues R356–R359; two potential N-glycosylation sites encompassing residues N44–C47 and N217–E220; 11 potential casein kinase II phosphorylation sites encompassing residues S11–E14, T28–D31, S117–D120, S118–D121, T205–D208, T295–E298, S325–D328, T351–E354, T402–E405, S432–D435, and T445–E448; and three potential protein kinase C phosphorylation sites encompassing residues S102–R104, S138–K140, and T449–K451. As shown in FIGS. 2A and 2B, HCDR-1 has chemical and structural homology with a mouse H5 protein (GI 51203; SEQ ID NO:7) and a human cell division control related protein (GI 1809317; SEQ ID NO:8). In particular, HCDR-1 and the mouse H5 protein share 92% sequence homology, HCDR-1 and the human cell division control related protein share 80% sequence homology. As illustrated by FIGS. 3A and 3B, HCDR-1 and the mouse H5 protein have rather similar hydrophobicity plots. Northern analysis shows the expression of HCDR-1 in various cDNA libraries, at least 34% of which are immortalized or cancerous, at least 20% of which involve immune response, and at least 14% are expressed in fetal/infant tissues or organs.

Nucleic acids encoding the HCDR-2 of the present invention were first identified in Incyte Clone 348429 from a ventricle tissue cDNA library (LVENNOT01) using a computer search for amino acid sequence alignments. A consensus sequence, SEQ ID NO:4, was derived from the following overlapping and/or extended nucleic acid sequences: Incyte Clones 407765 (EOSIHET02), 2265406 (UTRSNOT02), and 348429 (LVENNOT01).

Figure 6A:
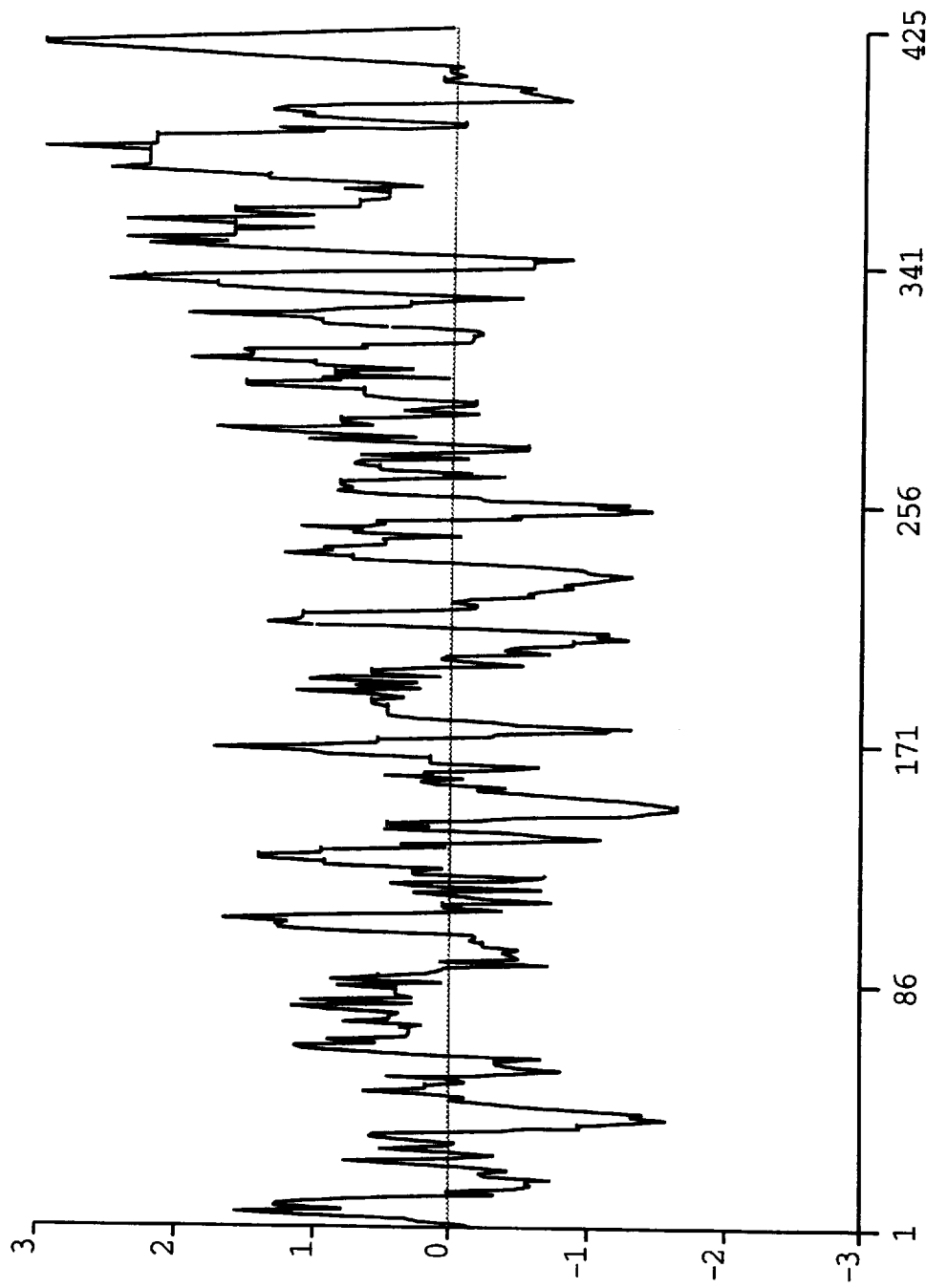
FIGS. 6A and 6B show the hydrophobicity plots for HCDR-2 (SEQ ID NO:3) and KIAA0128 (SEQ ID NO:9), respectively. The positive X axis reflects amino acid position, and the negative Y axis, hydrophobicity (MACDNASIS PRO software).
Figure 6B:
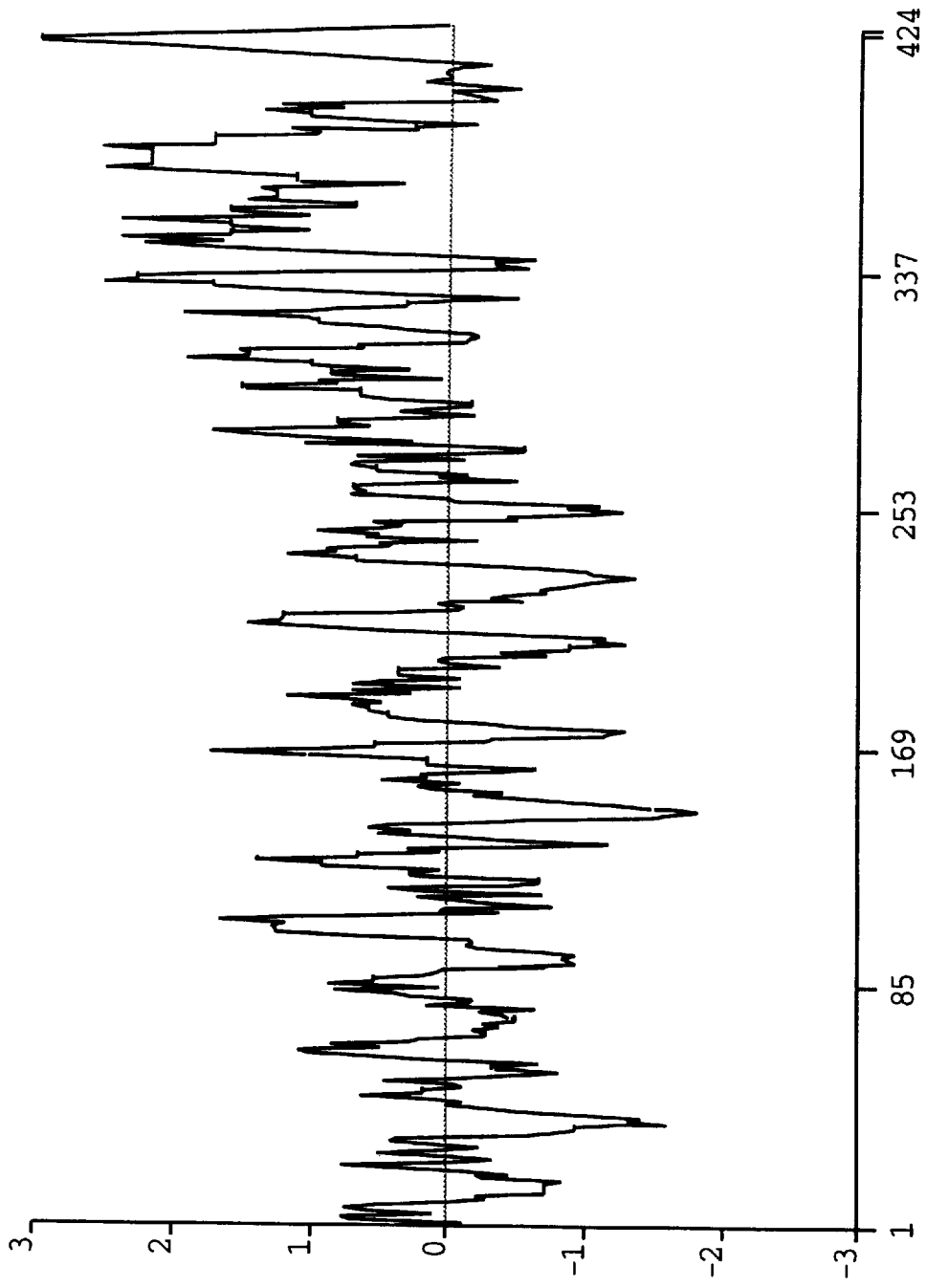

In one embodiment, the invention encompasses a polypeptide, HCDR-2, comprising the amino acid sequence of SEQ ID NO:3, as shown in FIGS. 4A, 4B, 4C, 4D, and 4E. HCDR-2 is 425 amino acids in length. It has a conserved ATP/GTP-binding site encompassing residues G48–S55. HCDR-2 has three potential N-glycosylation sites encompassing residues N15–L18, N33–T36, and N225–M228; 13 potential casein kinase II phosphorylation sites encompassing residues S9–E12, S26–D29, T56–D59, T64–E67, T72–E75, T97–D100, T216–E219, T220–E223, S239–E242, T310–D313, S318–E321, T373–E376, and T417–D420; and four potential protein kinase C phosphorylation sites encompassing residues S113–K115, S160–K162, T168–K170, and T417–K419. As shown in FIGS. 5A and 5B, HCDR-2 has chemical and structural homology with a human CDC10-related protein, KIAA0128 (GI 1469179; SEQ ID NO:9). In particular, HCDR-2 and KIAA0128 share 82% sequence homology. As illustrated by FIGS. 6A and 6B, HCDR-2 and KIAA0128 have rather similar hydrophobicity plots. Northern analysis shows the expression of HCDR-2 in various cDNA libraries, at least 38% of which are immortalized or cancerous, at least 14% of which involve immune response, and at least 24% are expressed in fetal/infant tissues or organs.

Nucleic acids encoding the HCDR-3 of the present invention were first identified in Incyte Clone 2458438 from a aortic endothelial cell cDNA library (ENDANOT01) using a computer search for amino acid sequence alignments. A consensus sequence, SEQ ID NO:6, was derived from the following overlapping and/or extended nucleic acid sequences: Incyte Clones 1287508 (BRAINOT11), 1747368

(STOMTUT02), 2636947 (BONTNOT01), 2635478 (BONTNOT01), 2325889 (OVARNOT02), and 2458438 (ENDANOT01).

Figure 9A:
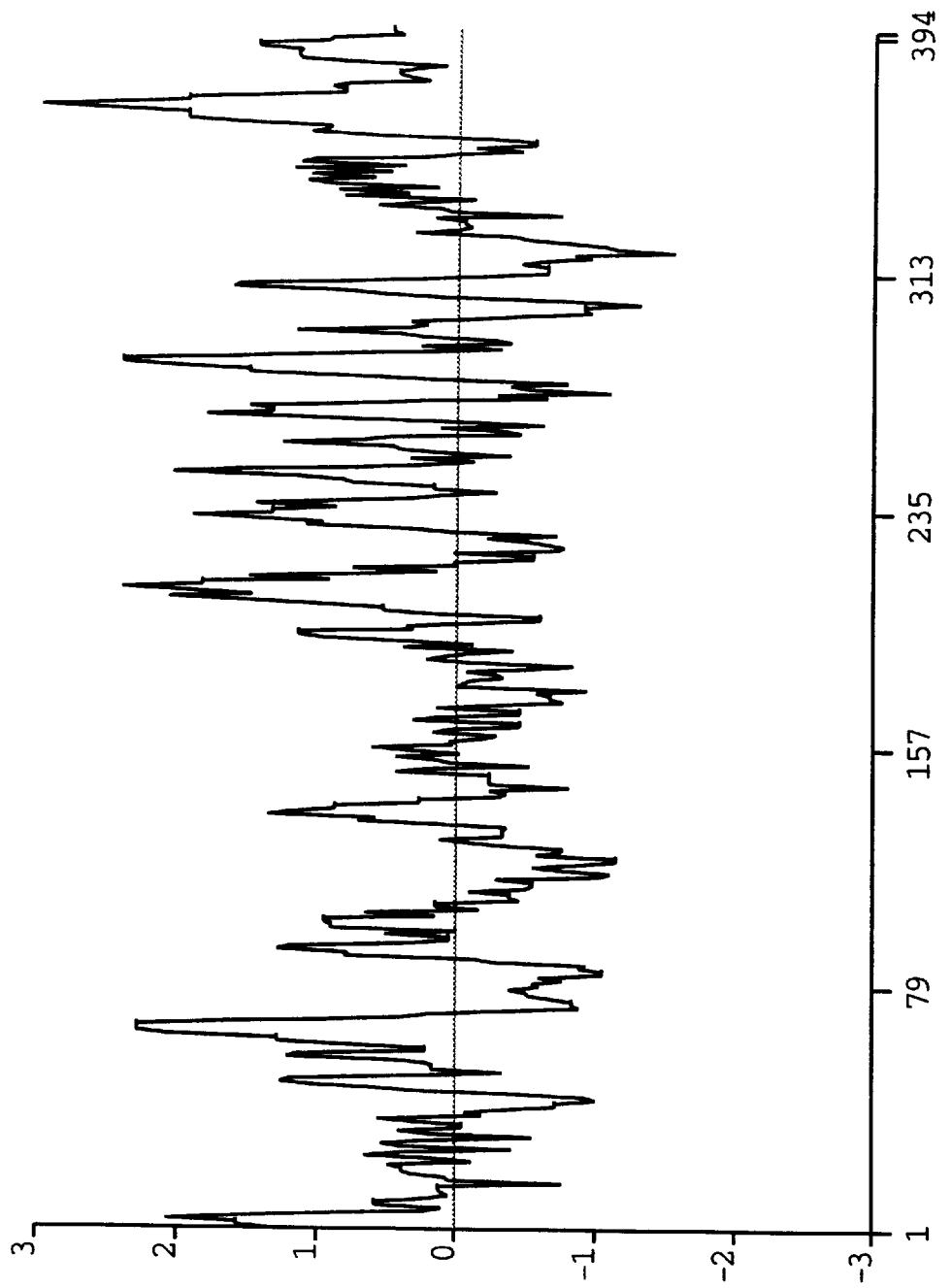
FIGS. 9A and 9B show the hydrophobicity plots for HCDR-3 (SEQ ID NO:5) and the mouse proliferation-associated protein 1 (SEQ ID NO:9), respectively. The positive X axis reflects amino acid position, and the negative Y axis, hydrophobicity (MACDNASIS PRO software).
Figure 9B:
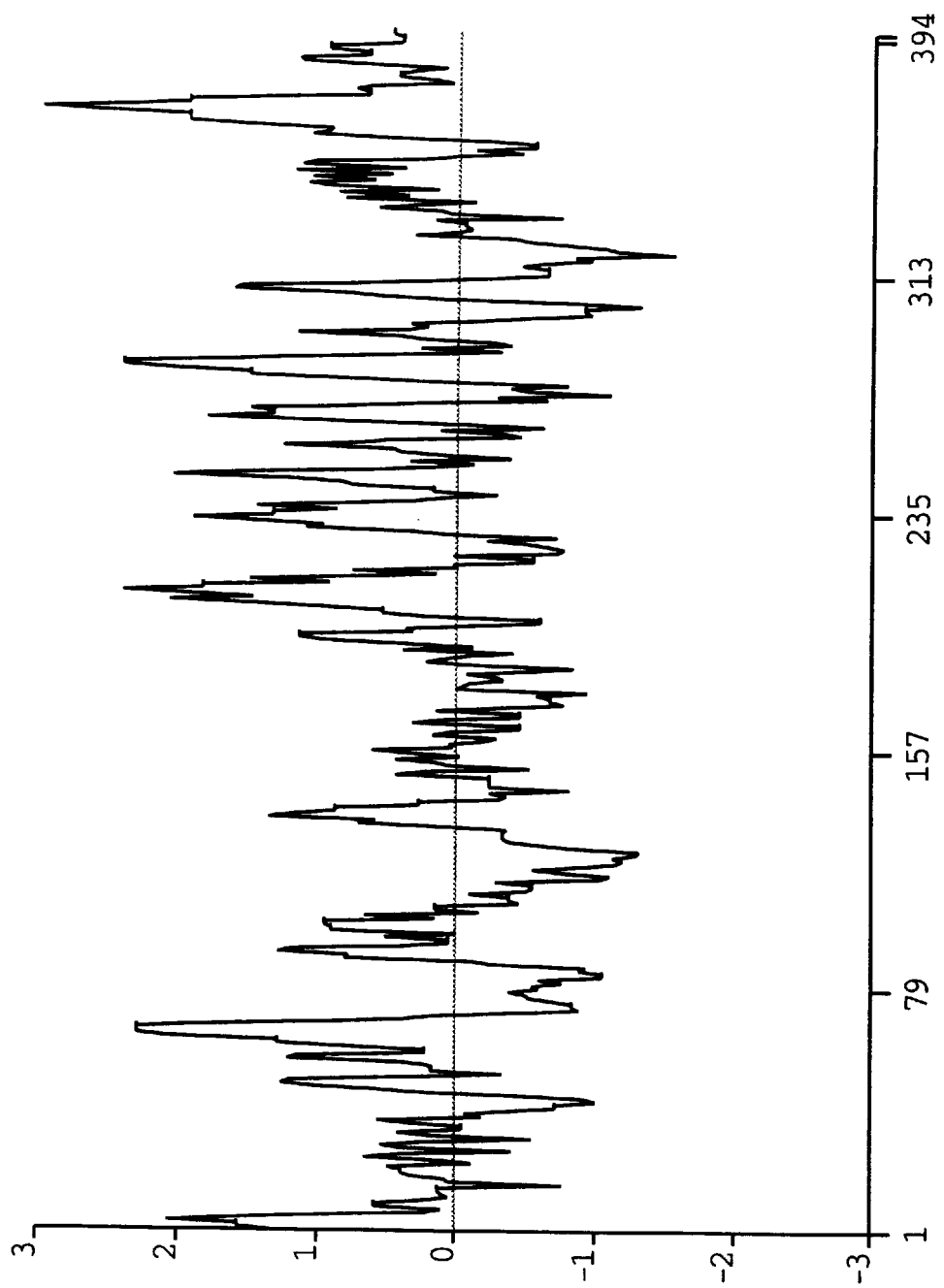

In one embodiment, the invention encompasses a polypeptide, HCDR-3, comprising the amino acid sequence of SEQ ID NO:5, as shown in FIGS. 7A, 7B, 7C, and 7D. HCDR-3 is 417 amino acids in length. HCDR-3 has one potential amidation site encompassing residues T136–K139; one potential N-glycosylation site encompassing residues N380–S383; one potential cAMP- and cGMP-dependent protein kinase phosphorylation site encompassing residues K372–S375; 11 potential casein kinase II phosphorylation sites encompassing residues S2–D5, T11–E14, S34–E37, S47–E50, S94–D97, T180–E183, S231–E234, S267–E270, S345–E348, T382–E385, and T386–E389; and six potential protein kinase C phosphorylation sites encompassing residues T60–K62, T136–R138, T261–R263, T279–R281, S363–K365, and T366–K369. As shown in FIGS. 8A and 8B, HCDR-3 has chemical and structural homology with mouse proliferation-associated protein 1 (GI 1167967; SEQ ID NO:10). In particular, HCDR and the mouse proliferation-associated protein 1 share 98% sequence homology. As illustrated by FIGS. 9A and 9B, HCDR-3 and the mouse protein have rather similar hydrophobicity plots. Northern analysis shows the expression of HCDR-3 in various cDNA libraries, at least 59% of which are immortalized or cancerous, at least 19% of which involve immune response, and at least 23% are expressed in fetal/infant tissues or organs.

The invention also encompasses HCDR variants. A preferred HCDR variant is one having at least 80%, and more preferably at least 90%, amino acid sequence identity to the HCDR amino acid sequence (SEQ ID NO:1, SEQ ID NO:3, or SEQ ID NO:5 ) and which retains at least one biological, immunological or other functional characteristic or activity of HCDR. A most preferred HCDR variant is one having at least 95% amino acid sequence identity to SEQ ID NO:1, SEQ ID NO:3, or SEQ ID NO:5.

The invention also encompasses polynucleotides which encode HCDR. Accordingly, any nucleic acid sequence which encodes the amino acid sequence of HCDR can be used to produce recombinant molecules which express HCDR. In a particular embodiment, the invention encompasses the polynucleotide comprising the nucleic acid sequence of SEQ ID NO:2, SEQ ID NO:4, or SEQ ID NO:6 as shown, respectively, in FIGS. 1A, 1B, 1C, 1D, and 1E; FIGS. 4A, 4B, 4C, 4D; and 4E, or FIGS. 7A, 7B, 7C, and 7D.

It will be appreciated by those skilled in the art that as a result of the degeneracy of the genetic code, a multitude of nucleotide sequences encoding HCDR, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring HCDR, and all such variations are to be considered as being specifically disclosed.

Although nucleotide sequences which encode HCDR and its variants are preferably capable of hybridizing to the nucleotide sequence of the naturally occurring HCDR under appropriately selected conditions of stringency, it may be advantageous to produce nucleotide sequences encoding HCDR or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HCDR and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode HCDR and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding HCDR or any fragment thereof.

Also encompassed by the invention are polynucleotide sequences that are capable of hybridizing to the claimed nucleotide sequences, and, in particular, those shown in SEQ ID NO:2, SEQ ID NO:4, or SEQ ID NO:6, under various conditions of stringency as taught in Wahl, G. M. and S. L. Berger (1987; Methods Enzymol. 152:399–407) and Kimmel, A. R. (1987; Methods Enzymol. 152:507–511).

Methods for DNA sequencing which are well known and generally available in the art may be used to practice any of the embodiments of the invention. The methods may employ such enzymes as the Klenow fragment of DNA polymerase I, SEQUENASE® (US Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE Amplification System marketed by Gibco/BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA Sequencers (Perkin Elmer).

The nucleic acid sequences encoding HCDR may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using commercially available software such as OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J .D. et al. (1991; Nucleic Acids Res. 19:3055–3060). Additionally, one may use PCR, nested primers, and PROMOTERFINDER™ libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER™ and SEQUENCE NAVIGATOR™, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode HCDR may be used in recombinant DNA molecules to direct expression of HCDR, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express HCDR.

As will be understood by those of skill in the art, it may be advantageous to produce HCDR-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter HCDR encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding HCDR may be ligated to a heterologous sequence to encode a fusion protein. For example, to screen peptide libraries for inhibitors of HCDR activity, it may be useful to encode a chimeric HCDR protein that can be recognized by a commercially available antibody. A fusion protein may also be engineered to contain a cleavage site located between the HCDR encoding sequence and the heterologous protein sequence, so that HCDR may be cleaved and purified away from the heterologous moiety.

In another embodiment, sequences encoding HCDR may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of HCDR, or a fragment thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) *Proteins, Structures and Molecular Principles,* W H Freeman and Co., New York, N.Y.). The composition of the synthetic peptides may be confirmed by amino acid analysis or sequencing (e.g., the Edman degradation procedure; Creighton, supra). Additionally, the amino acid sequence of HCDR, or any part thereof, may be altered during direct synthesis and/or combined using chemical methods with sequences from other proteins, or any part thereof, to produce a variant polypeptide.

In order to express a biologically active HCDR, the nucleotide sequences encoding HCDR or functional equivalents, may be inserted into an appropriate expression vector, i.e., a vector which contains the necessary elements for the transcription and translation of the inserted coding sequence.

Methods which are well known to those skilled in the art may be used to construct expression vectors containing sequences encoding HCDR and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual,* Cold Spring Harbor Press, Plainview, N.Y., and Ausubel, F. M. et al. (1989) *Current Protocols in Molecular Biology,* John Wiley & Sons, New York, N.Y.

A variety of expression vector/host systems may be utilized to contain and express sequences encoding HCDR. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT® phagemid (Stratagene, LaJolla, Calif.) or PSPORT1™ plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding HCDR, vectors based on SV40 or EBV may be used with an appropriate selectable marker.

In bacterial systems, a number of expression vectors may be selected depending upon the use intended for HCDR. For example, when large quantities of HCDR are needed for the induction of antibodies, vectors which direct high level expression of fusion proteins that are readily purified may be used. Such vectors include, but are not limited to, the multifunctional *E. coli* cloning and expression vectors such as BLUESCRIPT® (Stratagene), in which the sequence encoding HCDR may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae,* a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding HCDR may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196).

An insect system may also be used to express HCDR. For example, in one such system, *Autographa californica* nuclear polyhedrosis virus (AcNPV) is used as a vector to express foreign genes in *Spodoptera frugiperda* cells or in Trichoplusia larvae. The sequences encoding HCDR may be cloned into a non-essential region of the virus, such as the polyhedrin gene, and placed under control of the polyhedrin promoter. Successful insertion of HCDR will render the polyhedrin gene inactive and produce recombinant virus lacking coat protein. The recombinant viruses may then be used to infect, for example, *S. frugiperda* cells or Trichoplusia larvae in which HCDR may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding HCDR may be ligated into an adenovirus transcription/translation complex consisting of the late promoter and tripartite leader sequence. Insertion in a non-essential E1 or E3 region of the viral genome may be used to obtain a viable virus which is capable of expressing HCDR in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding HCDR. Such signals include the ATG initiation codon and adjacent sequences. In cases where sequences encoding HCDR, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express HCDR may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk$^-$ or aprt$^-$ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding HCDR is inserted within a marker gene sequence, transformed cells containing sequences encoding HCDR can be identified by the absence of marker gene function. Alternatively, a marker gene can be placed in tandem with a sequence encoding HCDR under the control of a single promoter. Expression of the marker gene in response to induction or selection usually indicates expression of the tandem gene as well.

Alternatively, host cells which contain the nucleic acid sequence encoding HCDR and express HCDR may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding HCDR can be detected by DNA-DNA or DNA-RNA hybridization or amplification using probes or fragments or fragments of polynucleotides encoding HCDR. Nucleic acid amplification based assays involve the use of oligonucleotides or oligomers based on the sequences encoding HCDR to detect transformants containing DNA or RNA encoding HCDR.

A variety of protocols for detecting and measuring the expression of HCDR, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on HCDR is preferred, but a competitive binding assay may be employed. These and other assays are described, among other places, in Hampton, R. et al. (1990; *Serological Methods, a Laboratory Manual,* APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HCDR include oligolabeling, nick translation, end-labeling or PCR amplification using a labeled nucleotide. Alternatively, the sequences encoding HCDR, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio)). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding HCDR may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode HCDR may be designed to contain signal sequences which direct secretion of HCDR through a prokaryotic or eukaryotic cell membrane. Other constructions may be used to join sequences encoding HCDR to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and HCDR may be used to facilitate purification. One such expression vector provides for expression of a fusion protein containing HCDR and a nucleic acid encoding 6 histidine residues preceding a thioredoxin or an enterokinase cleavage site. The histidine residues facilitate purification on IMAC (immobilized metal ion affinity chromatography) as described in Porath, J. et al. (1992, Prot. Exp. Purif. 3: 263–281) while the enterokinase cleavage site provides a means for purifying HCDR from the fusion protein. A discussion of vectors which contain fusion proteins is provided in Kroll, D. J. et al. (1993; DNA Cell Biol. 12:441–453).

In addition to recombinant production, fragments of HCDR may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using Applied Biosystems 431A Peptide Synthesizer (Perkin Elmer). Various fragments of HCDR may be chemically synthesized separately and combined using chemical methods to produce the full length molecule.

Therapeutics

Chemical and structural homology exists among HCDR-1, a mouse H5 protein (GI 51203; SEQ ID NO:7), and a human cell division control related protein (GI 1809317; SEQ ID NO:8); between HCDR-2 and a human CDC10-related protein, KIAA0128 (GI 1469179; SEQ ID NO:9); and between HCDR-3 and mouse proliferation-associated protein 1 (GI 1167967; SEQ ID NO: 10). Northern analysis shows that the expression of HCDR (SEQ ID NO:1, SEQ ID NO:3, or SEQ ID NO:5) is associated with cancer and fetal/infant development. Therapeutic uses for all three polypeptides are described collectively below.

During fetal development, decreased expression of HCDR may cause an increase in apoptosis with no adverse effects to the subject. However, in other situations and in adults, decreased expression of HCDR may cause an increase in apoptosis which is detrimental. Therefore, in one embodiment, HCDR or a fragment or derivative thereof may be administered to a subject to prevent or treat a disorder associated with an increase in apoptosis. Such disorders include, but are not limited to, AIDS and other infectious or genetic immunodeficiencies, neurodegenerative diseases such as Alzheimer's disease, Parkinson's disease, amyotrophic lateral sclerosis, retinitis pigmentosa, and cerebellar degeneration, myelodysplastic syndromes such as aplastic anemia, ischemic injuries such as myocardial infarction, stroke, and reperfusion injury, toxin-induced diseases such as alcohol-induced liver damage, cirrhosis, and lathyrism, wasting diseases such as cachexia, viral infections such as those caused by hepatitis B and C, and osteoporosis.

In another embodiment, a pharmaceutical composition comprising HCDR may be administered to a subject to prevent or treat a disorder associated with increased apoptosis including, but not limited to, those listed above.

In still another embodiment, an agonist which is specific for HCDR may be administered to prevent or treat a disorder associated with increased apoptosis including, but not limited to, those listed above.

In still another embodiment, a vector capable of expressing HCDR, or a fragment or a derivative thereof, may be used to prevent or treat a disorder associated with increased apoptosis including, but not limited to, those listed above.

In a further embodiment, HCDR or a fragment or derivative thereof may be added to cells to stimulate cell proliferation. In particular, HCDR may be added to a cell or cells in vivo using delivery mechanisms such as liposomes, viral based vectors, or electroinjection for the purpose of promoting regeneration or cell differentiation of the cell or cells. In addition, HCDR may be added to a cell, cell line, tissue or organ culture in vitro or ex vivo to stimulate cell proliferation for use in heterologous or autologous transplantation. In some cases, the cell will have been selected for its ability to fight an infection or a cancer or to correct a genetic defect in a disease such as sickle cell anemia, β thalassemia, cystic fibrosis, or Huntington's chorea.

In another further embodiment, an agonist which is specific for HCDR may be administered to a cell to stimulate cell proliferation, as described above.

In another further embodiment, a vector capable of expressing HCDR, or a fragment or a derivative thereof, may be administered to a cell or cells in vivo using delivery mechanisms, or to a cell to stimulate cell proliferation, as described above.

Increased expression of HCDR appears to be associated with increased cell proliferation. Therefore, in one embodiment, an antagonist of HCDR, or a fragment or a derivative thereof, may be administered to a subject to prevent or treat a disorder associated with cell proliferation. Such disorders include various types of cancer including, but not limited to, adenocarcinoma, leukemia, lymphoma, melanoma, myeloma, sarcoma, and teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody specific for HCDR may be used directly as an antagonist, or indirectly as a targeting or delivery mechanism for bringing a pharmaceutical agent to cells or tissue which express HCDR.

In still another embodiment, a vector expressing the complement of the polynucleotide encoding HCDR, or a fragment or a derivative thereof, may be administered to a subject to prevent or treat a disorder associated with cell proliferation including, but not limited to, the types of cancer listed above.

In another embodiment, an antagonist of HCDR, or a fragment or a derivative thereof, may be administered to a subject to prevent or treat an inflammation. Disorders associated with inflammation include, but are not limited to, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections and trauma. In one aspect, an antibody specific for HCDR may be used directly as an antagonist, or indirectly as a targeting or delivery mechanism for bringing a pharmaceutical agent to cells or tissue which express HCDR.

In still another embodiment, a vector expressing the complement of the polynucleotide encoding HCDR, or a fragment or a derivative thereof, may be administered to a subject to prevent or treat an inflammation associated with any disorder including, but not limited to, those listed above.

In other embodiments, any of the proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of HCDR may be produced using methods which are generally known in the art. In particular, purified HCDR may be used to produce antibodies or to screen libraries of pharmaceutical agents to identify those which specifically bind HCDR.

Antibodies to HCDR may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with HCDR or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to HCDR have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of HCDR amino acids may be fused with those of another protein such as keyhole limpet hemocyanin and antibody produced against the chimeric molecule.

Monoclonal antibodies to HCDR may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce HCDR-specific single chain antibodies. Antibodies with related specificity, but of distinct idiotypic composition, may be generated by chain shuffling from random combinatorial immunoglobin libraries (Burton D. R. (1991) Proc. Natl. Acad. Sci. 88:11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349:293–299).

Antibody fragments which contain specific binding sites for HCDR may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HCDR and its specific antibody. A two-site, monoclonal-based immunoassay utilizing monoclonal antibodies reactive to two non-interfering HCDR epitopes is preferred, but a competitive binding assay may also be employed (Maddox, supra).

In another embodiment of the invention, the polynucleotides encoding HCDR, or any fragment or complement thereof, may be used for therapeutic purposes. In one aspect, the complement of the polynucleotide encoding HCDR may be used in situations in which it would be desirable to block the transcription of the mRNA. In particular, cells may be transformed with sequences complementary to polynucleotides encoding HCDR. Thus, complementary molecules or fragments may be used to modulate HCDR activity, or to achieve regulation of gene function. Such technology is now well known in the art, and sense or antisense oligonucleotides or larger fragments, can be designed from various locations along the coding or control regions of sequences encoding HCDR.

Expression vectors derived from retro viruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding HCDR. These techniques are described both in Sambrook et al. (supra) and in Ausubel et al. (supra).

Genes encoding HCDR can be turned off by transforming a cell or tissue with expression vectors which express high levels of a polynucleotide or fragment thereof which encodes HCDR. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5' or regulatory regions of the gene encoding HCDR (signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding HCDR.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HCDR. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15:462–66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of HCDR, antibodies to HCDR, mimetics, agonists, antagonists, or inhibitors of HCDR. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of HCDR, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example HCDR or fragments thereof, antibodies of HCDR, agonists, antagonists or inhibitors of HCDR, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, ED50/LD50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind HCDR may be used for the diagnosis of conditions or diseases characterized by expression of HCDR, or in assays to monitor patients being treated with HCDR, agonists, antagonists or inhibitors. The antibodies useful for diagnostic purposes may be prepared in the same manner as those described above for therapeutics. Diagnostic assays for HCDR include methods which utilize the antibody and a label to detect HCDR in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring HCDR are known in the art and provide a basis for diagnosing altered or abnormal levels of HCDR expression. Normal or standard values for HCDR expression are established by combining body fluids or cell extracts taken from normal mammalian subjects, preferably human, with antibody to HCDR under conditions suitable for complex formation. The amount of standard complex formation may be quantified by various methods, but preferably by photometric means. Quantities of HCDR expressed in subject, control, and disease, samples from biopsied tissues are compared with the standard values. Deviation between standard and subject values establishes the parameters for diagnosing disease.

In another embodiment of the invention, the polynucleotides encoding HCDR may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of HCDR may be correlated with disease. The diagnostic assay may be used to distinguish between absence, presence, and excess expression of HCDR, and to monitor regulation of HCDR levels during therapeutic intervention.

In one aspect, hybridization with PCR probes which are capable of detecting polynucleotide sequences, including genomic sequences, encoding HCDR or closely related molecules, may be used to identify nucleic acid sequences which encode HCDR. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding HCDR, alleles, or related sequences.

Probes may also be used for the detection of related sequences, and should preferably contain at least 50% of the nucleotides from any of the HCDR encoding sequences. The hybridization probes of the subject invention may be DNA or RNA and derived from the nucleotide sequence of SEQ ID NO:2, SEQ ID NO:4, SEQ ID NO:6, or from genomic sequence including promoter, enhancer elements, and introns of the naturally occurring HCDR.

Means for producing specific hybridization probes for DNAs encoding HCDR include the cloning of nucleic acid sequences encoding HCDR or HCDR derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding HCDR may be used for the diagnosis of conditions or disorders which are associated with expression of HCDR. Examples of such conditions or disorders include, but are not limited to, disorders associated with cell proliferation such as adenocarcinoma, leukemia, lymphoma, melanoma, myeloma, sarcoma, and teratocarcinoma, and particularly, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; disorders with associated inflammation such as Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections and trauma; disorders with associated apoptosis such as AIDS and other infectious or genetic immunodeficiencies, neurodegenerative diseases such as Alzheimer's disease, Parkinson's disease, amyotrophic lateral sclerosis, retinitis pigmentosa, and cerebellar degeneration, myelodysplastic syndromes such as aplastic anemia, ischemic injuries such as myocardial infarction, stroke, and reperfusion injury, toxin-induced diseases such as alcohol-induced liver damage, cirrhosis, and lathyrism, wasting diseases such as cachexia, viral infections such as those caused by hepatitis B and C, and osteoporosis. The polynucleotide sequences encoding HCDR may be used in Southern or northern analysis, dot blot, or other membrane-based technologies; in PCR technologies; or in dipstick, pin, ELISA assays or microarrays utilizing fluids or tissues from patient biopsies to detect altered HCDR expression. Such qualitative or quantitative methods are well known in the art.

In a particular aspect, the nucleotide sequences encoding HCDR may be useful in assays that detect activation or induction of various cancers, particularly those mentioned above. The nucleotide sequences encoding HCDR may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding HCDR in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of HCDR, a normal or standard profile for expression is established. This may be accomplished by combining body fluids or cell extracts taken from normal subjects, either animal or human, with a sequence, or a fragment thereof, which encodes HCDR, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding HCDR may involve the use of PCR. Such oligomers may be chemically synthesized, generated enzymatically, or produced in vitro. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of HCDR include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or colorimetric response gives rapid quantitation.

In further embodiments, an oligonucleotide derived from any of the polynucleotide sequences described herein may be used as a target in a microarray. The microarray can be used to monitor the expression level of large numbers of genes simultaneously (to produce a transcript image), and to identify genetic variants, mutations and polymorphisms. This information will be useful in determining gene function, understanding the genetic basis of disease, diagnosing disease, and in developing and monitoring the activity of therapeutic agents (Heller, R. et al. (1997) Proc. Natl. Acad. Sci. 94:2150–55).

In one embodiment, the microarray is prepared and used according to the methods described in PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray, it may be preferable to use oligonucleotides which are only 7–10 nucleotides in length. The microarray may contain oligonucleotides which cover the known 5', or 3', sequence, sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell type, developmental or disease state.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. In certain situations it may be appropriate to use pairs of oligonucleotides on a microarray. The "pairs" will be identical, except for one nucleotide which preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536 or 6144 oligonucleotides, or any other number between two and one million which lends itself to the efficient use of commercially available instrumentation.

In order to conduct sample analysis using a microarray, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large scale correlation studies on the sequences, mutations, variants, or polymorphisms among samples.

In another embodiment of the invention, the nucleic acid sequences which encode HCDR may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial P1 constructions or single chromosome cDNA libraries as reviewed in Price, C. M. (1993) Blood Rev. 7:127–134, and Trask, B. J. (1991) Trends Genet. 7:149–154.

Fluorescent in situ hybridization (FISH as described in Verma et al. (1988) *Human Chromosomes: A Manual of Basic Techniques,* Pergamon Press, New York, N.Y.) may be correlated with other physical chromosome mapping techniques and genetic map data. Examples of genetic map data can be found in various scientific journals or at Online Mendelian Inheritance in Man (OMIM). Correlation between the location of the gene encoding HCDR on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, HCDR, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between HCDR and the agent being tested, may be measured.

Another technique for drug screening which may be used provides for high throughput screening of compounds having suitable binding affinity to the protein of interest as described in published PCT application WO84/03564. In this method, as applied to HCDR, large numbers of different small test compounds are synthesized on a solid substrate, such as plastic pins or some other surface. The test compounds are reacted with HCDR, or fragments thereof, and washed. Bound HCDR is then detected by methods well known in the art. Purified HCDR can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HCDR specifically compete with a test compound for binding HCDR. In this manner, the antibodies can be used to detect the presence of any peptide which shares one or more antigenic determinants with HCDR.

In additional embodiments, the nucleotide sequences which encode HCDR may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I cDNA Library Construction

The human spleen cell cDNA library, SPLNFET01, was custom constructed by Stratagene. The tissue for the SPLNFET01 library was obtained from fetal spleens pooled from different sources and contained many different types of cells. The tissue for Poly(A+) RNA (mRNA) was purified, and cDNA was synthesized from the mRNA. Synthetic adaptor oligonucleotides were ligated onto cDNA ends enabling its insertion into UNI-ZAP™ vector system (Stratagene), allowing high efficiency unidirectional (sense orientation) lambda library construction and the convenience of a plasmid system with blue/white color selection to detect clones with cDNA insertions. Alternative unidirectional vectors are pcDNA1 (Invitrogen, San Diego Calif.) and pSH1ox-1 (Novagen, Madison Wis.).

The custom-constructed library phage particles were transfected into *E. coli* host strain XL1-BLUE® (Stratagene), which has a high transformation efficiency, increasing the probability of obtaining rare, underrepresented clones in the cDNA library.

The LVENNOT01 cDNA library was constructed from the left ventricle of a 51-year-old Caucasian female. The tissue was frozen, ground, and lysed immediately in buffer containing guanidinium isothiocyanate and spun through cesium chloride. The precipitate was treated by several phenol chloroform extractions and ethanol precipitations at pH 8. The resulting sample was DNased, and the polyadenylated mRNA was then isolated and purified using Qiagen OLIGOTEX (Qiagen, Chatsworth, Calif.).

First strand cDNA synthesis was accomplished using an oligo d(T) primer/linker which also contained an XhoI restriction site. Second strand synthesis was performed using a combination of DNA polymerase I, *E. coli* ligase, and RNase H, followed by the addition of an EcoRI adaptor to the blunt ended cDNA. The EcoRI adapted, double-stranded cDNA was then digested with XhoI restriction enzyme and fractionated to obtain sequences which exceeded 800 bp in size. The cDNAs were inserted into the LAMBDAZAP® vector system (Stratagene). The vector which contained the PBLUESCRIPT™ phagemid (Stratagene) was then transformed into *E. coli* host cells strain XL1-BLUEMRF® (Stratagene).

The ENDANOT01 cDNA library was constructed from an aortic endothelial cell line derived from explanted heart/aorta tissue obtained from a male. The frozen tissue was homogenized and lysed using a Brinkmann Homogenizer Polytron PT-3000 (Brinkmann Instruments, Westbury, N.J.) in guanidinium isothiocyanate solution. The lysate was centrifuged over a 5.7M CsCl cushion using a Beckman SW28 rotor in a Beckman L8-70M Ultracentrifuge (Beckman Instruments) for 18 hours at 25,000 rpm at ambient temperature. The RNA was extracted with acid phenol pH 4.7, precipitated using 0.3M sodium acetate and 2.5 volumes of ethanol, resuspended in RNAse-free water, and DNase treated at 37° C. RNA extraction and precipitation were repeated as before. The mRNA was then isolated using the QIAGEN OLIGOTEX kit (QIAGEN) and used to construct the cDNA libraries.

The mRNA was handled according to the recommended protocols in the SuperScript Plasmid System for cDNA Synthesis and Plasmid Cloning (Cat. #18248-013, Gibco/BRL). cDNAs were fractionated on a Sepharose CL4B column (Cat. #275105-01, Pharmacia), and those cDNAs exceeding 400 bp were ligated into pINCY 1. The plasmid pINCY 1 was subsequently transformed into DH5α™ competent cells (Cat. #18258-012, Gibco/BRL).

II Isolation and Sequencing of cDNA Clones

The phagemid forms of individual cDNA clones for SPLNFET01 or LVENNOT01 were obtained by the in vivo excision process, in which the host bacterial strain was coinfected with both the lambda library phage and an f1 helper phage. Proteins derived from both the library-containing phage and the helper phage nicked the lambda DNA, initiated new DNA synthesis from defined sequences on the lambda target DNA and created a smaller, single stranded circular phagemid DNA molecule that included all DNA sequences of the PBLUESCRIPT® plasmid and the cDNA insert. The phagemid DNA was secreted from the cells and purified, then used to re-infect fresh host cells, where the double stranded phagemid DNA was produced. Because the phagemid carries the gene for β-lactamase, the newly-transformed bacteria were selected on medium containing ampicillin.

Phagemid DNA was purified using the QIAWELL TR-8 Plasmid, QIAWELL PLUS DNA, or QIAWELL ULTRA DNA purification system (QIAGEN). This product line provides a convenient, rapid and reliable high-throughput method to lyse bacterial cells and isolate highly purified phagemid DNA using QIAGEN anion-exchange resin particles with EMPORE™ membrane technology (3M, Minneapolis, Minn.) in a multiwell format. The DNA was eluted from the purification resin already prepared for DNA sequencing and other analytical manipulations.

Plasmid cDNA for ENDANOT01 was released from the cells and purified using the REAL Prep 96 Plasmid Kit (Catalog #26173, QIAGEN). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, Gibco/BRL) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced according to the method of Sanger et al. (1975, J. Mol. Biol. 94:441f), using the Perkin Elmer Catalyst 800 or a Hamilton Micro Lab 2200 (Hamilton, Reno, Nev.) in combination with Peltier Thermal Cyclers (PTC200 from M J Research, Watertown, Mass.) and Applied Biosystems 377 DNA Sequencing Systems or the Perkin Elmer 373 DNA Sequencing System and the reading frame was determined.

III Homology Searching of cDNA Clones and Their Deduced Proteins

The nucleotide sequences of the Sequence Listing or amino acid sequences deduced from them were used as query sequences against databases such as GenBank, SwissProt, BLOCKS, and Pima II. These databases which contain previously identified and annotated sequences were searched for regions of homology (similarity) using BLAST, which stands for Basic Local Alignment Search Tool (Altschul SF (1993) J. Mol. Evol. 36:290–300; Altschul, SF et al. (1990) J. Mol. Biol. 215:403–10).

BLAST produces alignments of both nucleotide and amino acid sequences to determine sequence similarity. Because of the local nature of the alignments, BLAST is especially useful in determining exact matches or in identifying homologs which may be of prokaryotic (bacterial) or eukaryotic (animal, fungal or plant) origin. Other algorithms such as the one described in Smith R F and T F Smith (1992 Protein Engineering 5:35–51), incorporated herein by reference, can be used when dealing with primary sequence patterns and secondary structure gap penalties. As disclosed in this application, the sequences have lengths of at least 49 nucleotides, and no more than 12% uncalled bases (where N is recorded rather than A, C, G, or T).

The BLAST approach, as detailed in Karlin and Altschul (1993; Proc Nat Acad Sci 90:5873–7) and incorporated herein by reference, searches matches between a query sequence and a database sequence, to evaluate the statistical significance of any matches found, and to report only those matches which satisfy the user-selected threshold of significance. In this application, threshold was set at $10^{-25}$ for nucleotides and $10^{-14}$ for peptides.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. (1993) J. Mol. Evol. 36:290–300; Altschul, S. F. et al. (1990) J. Mol. Evol. 215:403–410) are used to search for identical or related molecules in nucleotide databases such as GenBank or the LIFESEQ™ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding HCDR occurs. Abundance and percent abundance are also reported. Abundance directly reflects the number of times a particular transcript is represented in a cDNA library, and percent abundance is abundance divided by the total number of sequences examined in the cDNA library.

V Extension of HCDR Encoding Polynucleotides

The nucleic acid sequence of the Incyte Clones 26459, 348429, or 2458438 was used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence "outward" generating amplicons containing new, unknown nucleotide sequence for the region of interest. The initial primers were designed from the cDNA using OLIGO 4.06 (National Biosciences), or another appropriate program, to be about 22 to about 30 nucleotides in length, to have a GC content of 50% or more, and to anneal to the target sequence at temperatures of about 68° to about 72° C. Any stretch of nucleotides which would result in hairpin structures and primer-primer dimerizations was avoided.

Selected human cDNA libraries (Gibco/BRL) were used to extend the sequence. If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. Beginning with 40 pmol of each primer and the recommended concentrations of all other components of the kit, PCR was performed using the Peltier Thermal Cycler (PTC200; M. J. Research, Watertown, Mass.) and the following parameters:

Step 1
94° C. for 1 min (initial denaturation)
Step 2
65° C. for 1 min
Step 3
68° C. for 6 min
Step 4
94° C. for 15 sec
Step 5
65° C. for 1 min
Step 6
68° C. for 7 min
Step 7
Repeat step 4–6 for 15 additional cycles
Step 8
94° C. for 15 sec
Step 9
65° C. for 1 min
Step 10
68° C. for 7:15 min
Step 11
Repeat step 8–10 for 12 cycles
Step 12
72° C. for 8 min
Step 13
4° C. (and holding)

A 5–10 µl aliquot of the reaction mixture was analyzed by electrophoresis on a low concentration (about 0.6–0.8%) agarose mini-gel to determine which reactions were successful in extending the sequence. Bands thought to contain the largest products were excised from the gel, purified using QIAQUICK™ (QIAGEN Inc., Chatsworth, Calif.), and trimmed of overhangs using Klenow enzyme to facilitate religation and cloning.

After ethanol precipitation, the products were redissolved in 13 µl of ligation buffer) 1 µl T4-DNA ligase (15 units) and 1 µl T4 polynucleotide kinase were added, and the mixture was incubated at room temperature for 2–3 hours or overnight at 16° C. Competent *E. coli* cells (in 40 µl of appropriate media) were transformed with 3 µl of ligation mixture and cultured in 80 µl of SOC medium (Sambrook et al., supra). After incubation for one hour at 37° C., the *E. coli* mixture was plated on Luria Bertani (LB)-agar (Sambrook et al., supra) containing 2x Carb. The following day, several colonies were randomly picked from each plate and cultured in 150 µl of liquid LB/2x Carb medium placed in an individual well of an appropriate, commercially-available, sterile 96-well microtiter plate. The following day, 5 µl of each overnight culture was transferred into a non-sterile 96-well plate and after dilution 1:10 with water, 5 µl of each sample was transferred into a PCR array.

For PCR amplification, 18 µl of concentrated PCR reaction mix (3.3x) containing 4 units of rTth DNA polymerase, a vector primer, and one or both of the gene specific primers used for the extension reaction were added to each well. Amplification was performed using the following conditions:

Step 1
94° C. for 60 sec
Step 2
94° C. for 20 sec
Step 3
55° C. for 30 sec
Step 4
72° C. for 90 sec
Step 5
Repeat steps 2–4 for an additional 29 cycles
Step 6
72° C. for 180 sec
Step 7
4° C. (and holding)

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2, SEQ ID NO:4, or SEQ ID NO:6 is used to obtain 5' regulatory sequences using the procedure above, oligonucleotides designed for 5' extension, and an appropriate genomic library.

VI Labeling and Use of Individual Hybridization Probes

Hybridization probes derived from SEQ ID NO:2, SEQ ID NO:4, or SEQ ID NO:6 are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 (National Biosciences), labeled by combining 50 pmol of each oligomer and 250 µCi of [$\gamma$-$^{32}$p] adenosine triphosphate (Amersham) and T4 polynucleotide kinase (DuPont NEN®, Boston, Mass.). The labeled oligonucleotides are substantially purified with Sephadex G-25 superfine resin column (Pharmacia & Upjohn). A aliquot containing $10^7$ counts per minute of the labeled probe is used in a typical membrane-based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1xsaline sodium citrate and 0.5% sodium dodecyl sulfate. After XOMAT AR™ film (Kodak, Rochester, N.Y.) is exposed to the blots in a Phosphoimager cassette (Molecular Dynamics, Sunnyvale, Calif.) for several hours, hybridization patterns are compared visually.

VII Microarrays

To produce oligonucleotides for a microarray, at least one of the nucleotide sequences described herein is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies 20 sequence-specific oligonucleotides of 20 nucleotides in length (20-mers). A matched set of oligonucleotides is created in which one nucleotide in the center of each sequence is altered. This process is repeated for each gene in the microarray, and double sets of twenty 20 mers are synthesized and arranged on the surface of the silicon chip using a light-directed chemical process (Chee, M. et al., PCT/WO95/11995, incorporated herein by reference).

In the alternative, a chemical coupling procedure and an ink jet device are used to synthesize oligomers on the surface of a substrate (Baldeschweiler, J. D. et al., PCT/WO95/25116, incorporated herein by reference). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. An array may be produced by hand or using available materials and machines and contain grids of 8 dots, 24 dots, 96 dots, 384 dots, 1536 dots or 6144 dots. After hybridization, the microarray is washed to remove nonhybridized probes, and a scanner is used to determine the levels and patterns of fluorescence. The scanned images are examined to determine degree of complementarity and the relative abundance of each oligonucleotide sequence on the micro-array.

VIII Complementary Polynucleotides

Sequence complementary to the HCDR-encoding sequence, or any part thereof, is used to decrease or inhibit expression of naturally occurring HCDR. Although use of oligonucleotides comprising from about 15 to about 30 base-pairs is described, essentially the same procedure is used with smaller or larger sequence fragments. Appropriate oligonucleotides are designed using Oligo 4.06 software and the coding sequence of HCDR, SEQ ID NO:1, SEQ ID NO:3, or SEQ ID NO:5. To inhibit transcription, a complementary oligonucleotide is designed from the most unique 5' sequence and used to prevent promoter binding to the coding sequence. To inhibit translation, a complementary oligonucleotide is designed to prevent ribosomal binding to the HCDR-encoding transcript.

IX Expression of HCDR

Expression of HCDR is accomplished by subcloning the cDNAs into appropriate vectors and transforming the vectors into host cells. In this case, the cloning vector is also used to express HCDR in *E. coli*. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of HCDR into the bacterial growth media which can be used directly in the following assay for activity.

X Demonstration of HCDR Activity

HCDR can be expressed by transforming a mammalian cell line such as COS7, HeLa or CHO with an eukaryotic expression vector encoding HCDR. Eukaryotic expression vectors are commercially available, and the techniques to introduce them into cells are well known to those skilled in the art. The cells are incubated for 48–72 hours after transformation under conditions appropriate for the cell line to allow expression of HCDR. Then, phase microscopy is used to compare the mitotic index of transformed versus control cells. An increase in the mitotic index indicates HCDR activity.

XI Production of HCDR Specific Antibodies

HCDR that is substantially purified using PAGE electrophoresis (Sambrook, supra), or other purification techniques, is used to immunize rabbits and to produce antibodies using standard protocols. The amino acid sequence deduced from SEQ ID NO:2, SEQ ID NO:4, or SEQ ID NO:6 is analyzed using DNASTAR software (DNASTAR Inc) to determine regions of high immunogenicity and a corresponding oligopeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio iodinated, goat anti-rabbit IgG.

XII Purification of Naturally Occurring HCDR Using Specific Antibodies

Naturally occurring or recombinant HCDR is substantially purified by immunoaffinity chromatography using antibodies specific for HCDR. An immunoaffinity column is constructed by covalently coupling HCDR antibody to an activated chromatographic resin, such as CNBr-activated Sepharose (Pharmacia & Upjohn). After the coupling, the resin is blocked and washed according to the manufacturer's instructions.

Media containing HCDR is passed over the immunoaffinity column, and the column is washed under conditions that allow the preferential absorbance of HCDR (e.g., high ionic strength buffers in the presence of detergent). The column is eluted under conditions that disrupt antibody/HCDR binding (eg, a buffer of pH 2–3 or a high concentration of a chaotrope, such as urea or thiocyanate ion), and HCDR is collected.

XIII Identification of Molecules Which Interact with HCDR

HCDR or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled HCDR, washed and any wells with labeled HCDR complex are assayed. Data obtained using different concentrations of HCDR are used to calculate values for the number, affinity, and association of HCDR with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

---

What is claimed is:

1. An isolated and purified polynucleotide sequence encoding the amino acid sequence of SEQ ID No:1.

2. An isolated and purified composition comprising the polynucleotide sequence of claim 1.

3. An isolated and purified polynucleotide sequence which is completely complementary to the polynucleotide sequence of claim 1.

4. An isolated and purified polynucleotide sequence comprising SEQ ID No:2.

5. A composition comprising the polynucleotide sequence of claim 4.

6. An isolated and purified polynucleotide sequence which is completely complementary to the polynucleotide sequence of claim 4.

7. An expression vector containing the polynucleotide sequence of claim 1.

8. A host cell containing the expression vector of claim 7.

9. A method for producing a polypeptide comprising the amino acid sequence of SEQ ID No:1, the method comprising the steps of.

a) culturing the host cell of claim 8 under conditions suitable for the expression of the polypeptide; and b) recovering the polypeptide from the host cell culture.

10. A method for detecting a polynucleotide which encodes a human cell division regulator in a biological sample, the method comprising the steps of:

a) hybridizing the polynucleotide of claim 3 to nucleic acid material in the biological sample, thereby forming a hybridization complex; and b) detecting the hybridization complex, wherein the presence of the hybridization complex correlates with the presence of a polynucleotide encoding the human cell division regulator in biological sample.

11. The method of claim 10 wherein the nucleic acid material is amplified by the polymerase chain reaction prior to hybridization.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 478 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: SPLNFZT01
        ( B ) CLONE: 26459

( x i ) SEQUENCE DESCRIPTION: SEQ ID NO:1:

```
Met  Asp  Arg  Ser  Leu  Gly  Trp  Gln  Gly  Asn  Ser  Val  Pro  Glu  Asp  Arg
  1              5                        10                       15

Thr  Glu  Ala  Gly  Ile  Lys  Arg  Phe  Leu  Glu  Asp  Thr  Thr  Asp  Asp  Gly
              20                       25                       30

Glu  Leu  Ser  Lys  Phe  Val  Lys  Asp  Phe  Ser  Gly  Asn  Ala  Ser  Cys  His
         35                       40                       45

Pro  Pro  Glu  Ala  Lys  Thr  Trp  Ala  Ser  Arg  Pro  Gln  Val  Pro  Glu  Pro
     50                       55                       60

Arg  Pro  Gln  Ala  Pro  Asp  Leu  Tyr  Asp  Asp  Asp  Leu  Glu  Phe  Arg  Pro
 65                      70                       75                       80

Pro  Ser  Arg  Pro  Gln  Ser  Ser  Asp  Asn  Gln  Gln  Tyr  Phe  Cys  Ala  Pro
                85                       90                       95

Ala  Pro  Leu  Ser  Pro  Ser  Ala  Arg  Pro  Arg  Ser  Pro  Trp  Gly  Lys  Leu
               100                      105                      110

Asp  Pro  Tyr  Asp  Ser  Ser  Glu  Asp  Asp  Lys  Glu  Tyr  Val  Gly  Phe  Ala
              115                      120                      125

Thr  Leu  Pro  Asn  Gln  Val  His  Arg  Lys  Ser  Val  Lys  Lys  Gly  Phe  Asp
     130                      135                      140

Phe  Thr  Leu  Met  Val  Ala  Gly  Glu  Ser  Gly  Leu  Gly  Lys  Ser  Thr  Leu
145                      150                      155                      160

Val  Asn  Ser  Leu  Phe  Leu  Ser  Asp  Leu  Tyr  Arg  Asp  Arg  Lys  Leu  Leu
               165                      170                      175

Gly  Ala  Glu  Glu  Arg  Ile  Met  Gln  Thr  Val  Glu  Ile  Thr  Lys  His  Ala
              180                      185                      190

Val  Asp  Ile  Glu  Glu  Lys  Gly  Val  Arg  Leu  Arg  Leu  Thr  Ile  Val  Asp
              195                      200                      205

Thr  Pro  Gly  Phe  Gly  Asp  Ala  Val  Asn  Asn  Thr  Glu  Cys  Trp  Lys  Pro
     210                      215                      220

Val  Ala  Glu  Tyr  Ile  Asp  Gln  Gln  Phe  Glu  Gln  Tyr  Phe  Arg  Asp  Glu
225                      230                      235                      240

Ser  Gly  Leu  Asn  Arg  Lys  Asn  Ile  Gln  Asp  Asn  Arg  Val  His  Cys  Cys
```

|     |     |     |     |     | 245 |     |     |     | 250 |     |     |     |     | 255 |     |
| --- | --- | --- | --- | --- | --- | --- | --- | --- | --- | --- | --- | --- | --- | --- | --- |
| Leu | Tyr | Phe | Ile | Ser | Pro | Phe | Gly | His | Gly | Leu | Arg | Pro | Leu | Asp | Val |
|     |     |     | 260 |     |     |     |     | 265 |     |     |     |     | 270 |     |     |
| Glu | Phe | Met | Lys | Ala | Leu | His | Gln | Arg | Val | Asn | Ile | Val | Pro | Ile | Leu |
|     |     |     | 275 |     |     |     |     | 280 |     |     |     |     | 285 |     |     |
| Ala | Lys | Ala | Asp | Thr | Leu | Thr | Pro | Pro | Glu | Val | Asp | His | Lys | Lys | Arg |
|     |     |     | 290 |     |     |     | 295 |     |     |     |     | 300 |     |     |     |
| Lys | Ile | Arg | Glu | Glu | Ile | Glu | His | Phe | Gly | Ile | Lys | Ile | Tyr | Gln | Phe |
| 305 |     |     |     |     | 310 |     |     |     |     | 315 |     |     |     |     | 320 |
| Pro | Asp | Cys | Asp | Ser | Asp | Glu | Asp | Glu | Asp | Phe | Lys | Leu | Gln | Asp | Gln |
|     |     |     |     | 325 |     |     |     |     | 330 |     |     |     |     | 335 |     |
| Ala | Leu | Lys | Glu | Ser | Ile | Pro | Phe | Ala | Val | Ile | Gly | Ser | Asn | Thr | Val |
|     |     |     |     | 340 |     |     |     |     | 345 |     |     |     |     | 350 |     |
| Val | Glu | Ala | Arg | Gly | Arg | Arg | Val | Arg | Gly | Arg | Leu | Tyr | Pro | Trp | Gly |
|     |     |     | 355 |     |     |     |     | 360 |     |     |     |     | 365 |     |     |
| Ile | Val | Glu | Val | Glu | Asn | Pro | Gly | His | Cys | Asp | Phe | Val | Lys | Leu | Arg |
|     |     |     | 370 |     |     |     | 375 |     |     |     |     | 380 |     |     |     |
| Thr | Met | Leu | Val | Arg | Thr | His | Met | Gln | Asp | Leu | Lys | Asp | Val | Thr | Arg |
| 385 |     |     |     |     | 390 |     |     |     |     | 395 |     |     |     |     | 400 |
| Glu | Thr | His | Tyr | Glu | Asn | Tyr | Arg | Ala | Gln | Cys | Ile | Gln | Ser | Met | Thr |
|     |     |     |     | 405 |     |     |     |     | 410 |     |     |     |     | 415 |     |
| Arg | Leu | Val | Val | Lys | Glu | Arg | Asn | Arg | Asn | Lys | Leu | Thr | Arg | Glu | Ser |
|     |     |     |     | 420 |     |     |     |     | 425 |     |     |     |     | 430 |     |
| Gly | Thr | Asp | Phe | Pro | Ile | Pro | Ala | Val | Pro | Pro | Gly | Thr | Asp | Pro | Glu |
|     |     |     |     | 435 |     |     |     |     | 440 |     |     |     |     | 445 |     |
| Thr | Glu | Lys | Leu | Ile | Arg | Glu | Lys | Asp | Glu | Glu | Leu | Arg | Arg | Met | Gln |
|     |     |     |     | 450 |     |     |     |     | 455 |     |     |     |     | 460 |     |
| Glu | Met | Leu | His | Lys | Ile | Gln | Lys | Gln | Met | Lys | Glu | Asn | Tyr |     |     |
| 465 |     |     |     |     | 470 |     |     |     |     | 475 |     |     |     |     |     |

( 2 ) INFORMATION FOR SEQ ID NO:2:

( i ) SEQUENCE CHARACTERISTICS:
        ( A ) LENGTH: 1816 base pairs
        ( B ) TYPE: nucleic acid
        ( C ) STRANDEDNESS: single
        ( D ) TOPOLOGY: linear ( v i i ) IMMEDIATE SOURCE:
        ( A ) LIBRARY: SPLNFZT01
        ( B ) CLONE: 26459

( x i ) SEQUENCE DESCRIPTION: SEQ ID NO:2:

| | | | | | |
|---|---|---|---|---|---|
| TGGGGTGGGG | AAGGACATTC | CACAGGCTTT | TTTGGCCCCT | GCCAGAGACA | GAAGGGGGTC | 60 |
| AAAGAGAAAG | GGAAAGGAGC | AAGCCAGGAA | GCCAGACAAC | AACAGCATCA | AACAAGGCT | 120 |
| GTTTCTGTGT | GTGAGGAACT | TTGCCTGGGA | GATAAAATTA | GACCTAGAGC | TTTCTGACAG | 180 |
| GGAGTCTGAA | GCGTGGGACA | TGGACCGTTC | ACTGGGATGG | CAAGGGAATT | CTGTCCCTGA | 240 |
| GGACAGGACT | GAAGCTGGGA | TCAAGCGTTT | CCTGGAGGAC | ACCACGGATG | ATGGAGAACT | 300 |
| GAGCAAGTTC | GTGAAGGATT | TCTCAGGAAA | TGCGAGCTGC | CACCCACCAG | AGGCTAAGAC | 360 |
| CTGGGCATCC | AGGCCCCAAG | TCCCGGAGCC | AAGGCCCCAG | GCCCCGGACC | TCTATGATGA | 420 |
| TGACCTGGAG | TTCAGACCCC | CCTCGCGGCC | CCAGTCCTCT | GACAACCAGC | AGTACTTCTG | 480 |
| TGCCCCAGCC | CCTCTCAGCC | CATCTGCCAG | GCCCCGCAGC | CCATGGGGCA | AGCTTGATCC | 540 |
| CTATGATTCC | TCTGAGGATG | ACAAGGAGTA | TGTGGGCTTT | GCAACCCTCC | CCAACCAAGT | 600 |
| CCACCGAAAG | TCCGTGAAGA | AAGGCTTTGA | CTTTACCCTC | ATGGTGGCAG | GAGAGTCTGG | 660 |

-continued

```
CCTGGGCAAA TCCACACTTG TCAATAGCCT CTTCCTCTCT GATCTGTACC GGGACCGGAA    720
ACTTCTTGGT GCTGAAGAGA GGATCATGCA AACTGTGGAG ATCACTAAGC ATGCAGTGGA    780
CATAGAAGAG AAGGGTGTGA GGCTGCGGCT CACCATTGTG GACACACCAG GTTTTGGGGA    840
TGCAGTCAAC AACACAGAGT GCTGGAAGCC TGTGGCAGAA TACATTGATC AGCAGTTTGA    900
GCAGTATTTC CGAGACGAGA GTGGCCTGAA CCGAAAGAAC ATCCAAGACA CAGGGTGCA     960
CTGCTGCCTG TACTTCATCT CACCCTTCGG CCATGGGCTC CGGCCATTGG ATGTTGAATT   1020
CATGAAGGCC CTGCATCAGC GGGTCAACAT CGTGCCTATC CTGGCTAAGG CAGACACACT   1080
GACACCTCCC GAAGTGGACC ACAAGAAACG CAAAATCCGG GAGGAGATTG AGCATTTTGG   1140
AATCAAGATC TATCAATTCC CAGACTGTGA CTCTGATGAG GATGAGGACT TCAAATTGCA   1200
GGACCAAGCC CTAAAGGAAA GCATCCCATT TGCAGTAATT GGCAGCAACA CTGTAGTAGA   1260
GGCCAGAGGG CGGCGAGTTC GGGGTCGACT CTACCCCTGG GGCATCGTGG AAGTGGAAAA   1320
CCCAGGGCAC TGCGACTTTG TGAAGCTGAG GACAATGCTG GTACGTACCC ACATGCAGGA   1380
CCTGAAGGAT GTGACACGGG AGACACATTA TGAGAACTAC CGGGCACAGT GCATCCAGAG   1440
CATGACCCGC CTGGTGGTGA AGGAACGGAA TCGCAACAAA CTGACTCGGG AAAGTGGTAC   1500
CGACTTCCCC ATCCCTGCTG TCCCACCAGG GACAGATCCA GAAACTGAGA AGCTTATCCG   1560
AGAGAAAGAT GAGGAGCTGC GGCGGATGCA GGAGATGCTA CACAAAATAC AAAAACAGAT   1620
GAAGGAGAAC TATTAACTGG CTTTCAGCCC TGGATATTTA AATCTCCTCC TCTTCTTCCT   1680
GTCCATGCCG GCCCCTCCCA GCACCAGCTC TGCTCAGGCC CCTTCAGCTA CTGCCACTTC   1740
GCCTTACATC CCTGCTGACT GCCCAGAGAC TCAGAGGAAA TAAAGTTTAA TAAATCTGTA   1800
GGTGGCAAAA AAAAAA                                                   1816
```

( 2 ) INFORMATION FOR SEQ ID NO:3:

( i ) SEQUENCE CHARACTERISTICS:
        ( A ) LENGTH: 425 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: LVZNNOT01
        ( B ) CLONE: 348429

( x i ) SEQUENCE DESCRIPTION: SEQ ID NO:3:

```
Met Ala Val Ala Val Gly Arg Pro Ser Asn Glu Glu Leu Arg Asn Leu
 1               5                  10                  15

Ser Leu Ser Gly His Val Gly Phe Asp Ser Leu Pro Asp Gln Leu Val
            20                  25                  30

Asn Lys Ser Thr Ser Gln Gly Phe Cys Phe Asn Ile Leu Cys Val Gly
        35                  40                  45

Glu Thr Gly Ile Gly Lys Ser Thr Leu Met Asp Thr Leu Phe Asn Thr
    50                  55                  60

Lys Phe Glu Ser Asp Pro Ala Thr His Asn Glu Pro Gly Val Arg Leu
65                  70                  75                  80

Lys Ala Arg Ser Tyr Glu Leu Gln Glu Ser Asn Val Arg Leu Lys Leu
                85                  90                  95

Thr Ile Val Asp Thr Val Gly Phe Gly Asp Gln Ile Asn Lys Asp Asp
            100                 105                 110

Ser Tyr Lys Pro Ile Val Glu Tyr Ile Asp Ala Gln Phe Glu Ala Tyr
        115                 120                 125
```

-continued

| Leu | Gln | Glu | Glu | Leu | Lys | Ile | Lys | Arg | Ser | Leu | Phe | Asn | Tyr | His | Asp |
|-----|-----|-----|-----|-----|-----|-----|-----|-----|-----|-----|-----|-----|-----|-----|-----|
| 130 | | | | | 135 | | | | | | 140 | | | | |

Thr Arg Ile His Ala Cys Leu Tyr Phe Ile Ala Pro Thr Gly His Ser
145                     150                     155                     160

Leu Lys Ser Leu Asp Leu Val Thr Met Lys Leu Asp Ser Val
                165                     170                     175

Asn Ile Ile Pro Ile Ile Ala Lys Ala Asp Thr Ile Ala Lys Asn Glu
                180                      185                      190

Leu His Lys Phe Lys Ser Lys Ile Met Ser Glu Leu Val Ser Asn Gly
                195                      200                      205

Val Gln Ile Tyr Gln Phe Pro Thr Asp Glu Glu Thr Val Ala Glu Ile
      210                      215                      220

Asn Ala Thr Met Ser Val His Leu Pro Phe Ala Val Val Gly Ser Thr
225                     230                     235                     240

Glu Glu Val Lys Ile Gly Asn Lys Met Ala Lys Ala Arg Gln Tyr Pro
                245                      250                      255

Trp Gly Val Val Gln Val Glu Asn Glu Asn His Cys Asp Phe Val Lys
                260                      265                      270

Leu Arg Glu Met Leu Ile Arg Val Asn Met Glu Asp Leu Arg Glu Gln
                275                      280                      285

Thr His Thr Arg His Tyr Glu Leu Tyr Arg Arg Cys Lys Leu Glu Glu
                290                      295                      300

Met Gly Phe Lys Asp Thr Asp Pro Asp Ser Lys Pro Phe Ser Leu Gln
305                     310                     315                     320

Glu Thr Tyr Glu Ala Lys Arg Asn Glu Phe Leu Gly Glu Leu Gln Lys
                325                      330                      335

Lys Glu Glu Glu Met Arg Gln Met Phe Val Met Arg Val Lys Glu Lys
                340                      345                      350

Glu Ala Glu Leu Lys Glu Ala Glu Lys Glu Leu His Glu Lys Phe Asp
                355                      360                      365

Leu Leu Lys Arg Thr His Gln Glu Glu Lys Lys Lys Val Glu Asp Lys
                370                      375                      380

Lys Lys Glu Leu Glu Glu Val Asn Asn Phe Gln Lys Lys Lys Ala
385                     390                     395                     400

Ala Ala Gln Leu Leu Gln Ser Gln Ala Gln Gln Ser Gly Ala Gln Gln
                     405                      410                      415

Thr Lys Lys Asp Lys Asp Lys Lys Asn
                420                      425

(2) INFORMATION FOR SEQ ID NO:4:

(i) SEQUENCE CHARACTERISTICS:
        (A) LENGTH: 1794 base pairs
        (B) TYPE: nucleic acid
        (C) STRANDEDNESS: single
        (D) TOPOLOGY: linear (vii) IMMEDIATE SOURCE:
        (A) LIBRARY: LVZNNOT01
        (B) CLONE: 348429

(xi) SEQUENCE DESCRIPTION: SEQ ID NO:4:

| GAGGCGCGAG | GGAGGCGAGC | CGGAGCCCGA | GCACTAGCAG | CAGCCGGAGT | CGGCGGAAAG | 60 |
| CACCCGGGCG | CACGGNAGAC | GGTGCCGCAG | CTGCGATGGC | CGTGGCCGTG | GGGAGACCGT | 120 |
| CTAATGAAGA | GCTTCGAAAC | TTGTCTTTGT | CTGGCCATGT | GGGATTTGAC | AGCCTCCCTG | 180 |
| ACCAGCTGGT | CAACAAGTCT | ACTTCTCAAG | GATTCTGTTT | CAACATCCTT | TGTGTTGGTG | 240 |

| | | | | | |
|---|---|---|---|---|---|
| AGACAGGCAT | TGGCAAATCC | ACGTTAATGG | ACACTTTGTT | CAACACCAAA | TTTGAAAGTG | 300 |
| ACCCAGCTAC | TCACAATGAA | CCAGGTGTTC | GGTTAAAAGC | CAGAAGTTAT | GAGCTTCAGG | 360 |
| AAAGCAATGT | ACGGCTGAAG | TTAACCATTG | TTGACACCGT | GGGATTTGGA | GACCAGATAA | 420 |
| ATAAAGATGA | CAGCTATAAG | CCGATAGTAG | AATATATTGA | TGCCCAGTTC | GAGGCCTACC | 480 |
| TGCAAGAGGA | ATTGAAGATT | AAACGTTCTC | TCTTCAACTA | CCATGACACG | AGGATCCATG | 540 |
| CCTGCCTCTA | CTTTATTGCC | CCTACTGGAC | ATTCACTAAA | GTCCCTGGAT | CTGGTCACCA | 600 |
| TGAAAAAGCT | GGACAGTAAG | GTGAACATCA | TTCCAATAAT | TGCAAAAGCT | GACACCATTG | 660 |
| CCAAGAATGA | ACTGCACAAA | TTCAAGAGTA | AGATCATGAG | TGAACTGGTC | AGCAATGGGG | 720 |
| TCCAGATATA | TCAGTTTCCC | ACTGATGAAG | AAACGGTGGC | AGAGATTAAC | GCAACAATGA | 780 |
| GTGTCCATCT | CCCATTTGCA | GTGGTTGGCA | GCACCGAAGA | GGTGAAGATT | GGCAACAAGA | 840 |
| TGGCAAAGGC | CAGGCAGTAC | CCCTGGGGTG | TGGTGCAGGT | TGAGAATGAA | AATCATTGCG | 900 |
| ATTTTGTGAA | ACTTCGAGAG | ATGCTGATCC | GCGTGAACAT | GGAGGACTTG | CGAGAGCAGA | 960 |
| CTCACACCCG | CCACTATGAA | TTGTACCGAC | GCTGTAAGCT | TGAAGAGATG | GGGTTCAAGG | 1020 |
| ACACTGACCC | TGACAGCAAA | CCCTTCAGTC | TTCAGGAGAC | ATATGAAGCA | AAAAGGAATG | 1080 |
| AATTCCTGGG | AGAACTGCAG | AAGAAAGAAG | AAGAAATGAG | ACAAATGTTT | GTTATGAGAG | 1140 |
| TGAAGGAGAA | AGAAGCTGAA | CTTAAGGAGG | CAGAGAAAGA | GCTTCACGAG | AAGTTTGACC | 1200 |
| TTCTAAAGCG | GACACACCAA | GAAGAAAAGA | AGAAAGTGGA | AGACAAGAAG | AAGGAGCTTG | 1260 |
| AGGAGGAGGT | GAACAACTTC | CAGAAGAAGA | AAGCAGCGGC | TCAGTACTA | CAGTCCCAGG | 1320 |
| CCCAGCAATC | TGGGGCCCAG | CAAACCAAGA | AAGACAAGGA | TAAGAAAAAC | TGACCATCTG | 1380 |
| CCTCTTGAGA | GAGAGAGAAG | TGGGCATCCT | TCCTTTAAAT | TCAGGAACCA | CTGTTGTTTT | 1440 |
| ATTTGACTTT | TTCTGTTACT | TGCATCCCTT | ATATAAGTTG | TTTTGGATTT | GGGACTATGT | 1500 |
| TTTGGGGGAG | AAAAACTCCA | GTTAGTTCTG | TTTTTTGTAT | TGGTTATTCA | GCTTACTTTT | 1560 |
| GGTATCAAAA | TTATGCCAGT | TTTAAGCTCA | CTTGAGTGAA | GTTTAAGTCA | CAAGATTCTG | 1620 |
| TTTAACATGC | TTTCCTTGTT | TTGGAAACAA | CCAAAAACTT | CCCTTTTTTG | TTACGGGATT | 1680 |
| TTGACCTACA | AATCCTAATC | ATGTTTAAAA | TGTGCCGGTG | TTGGGTAGAT | GACTTTTCTG | 1740 |
| CCTCTGGGGT | TCAATTTATA | TTTAAAGATA | CCTTAAAATA | AAAAAAAAG | AAAA | 1794 |

( 2 ) INFORMATION FOR SEQ ID NO:5:

( i ) SEQUENCE CHARACTERISTICS:
        ( A ) LENGTH: 394 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: ZNDANOT01
        ( B ) CLONE: 2458438

( x i ) SEQUENCE DESCRIPTION: SEQ ID NO:5:

| Met | Ser | Gly | Glu | Asp | Glu | Gln | Gln | Glu | Gln | Thr | Ile | Ala | Glu | Asp | Leu |
|---|---|---|---|---|---|---|---|---|---|---|---|---|---|---|---|
| 1 | | | | 5 | | | | | 10 | | | | | 15 | |

| Val | Val | Thr | Lys | Tyr | Lys | Met | Gly | Gly | Asp | Ile | Ala | Asn | Arg | Val | Leu |
|---|---|---|---|---|---|---|---|---|---|---|---|---|---|---|---|
| | | | 20 | | | | | 25 | | | | | 30 | | |

| Arg | Ser | Leu | Val | Glu | Ala | Ser | Ser | Ser | Gly | Val | Ser | Val | Leu | Ser | Leu |
|---|---|---|---|---|---|---|---|---|---|---|---|---|---|---|---|
| | | 35 | | | | | 40 | | | | | 45 | | | |

| Cys | Glu | Lys | Gly | Asp | Ala | Met | Ile | Met | Glu | Glu | Thr | Gly | Lys | Ile | Phe |
|---|---|---|---|---|---|---|---|---|---|---|---|---|---|---|---|
| | 50 | | | | | 55 | | | | | 60 | | | | |

| Lys | Lys | Glu | Lys | Glu | Met | Lys | Lys | Gly | Ile | Ala | Phe | Pro | Thr | Ser | Ile |
|---|---|---|---|---|---|---|---|---|---|---|---|---|---|---|---|

|  |  |  |  | 65 |  |  |  |  | 70 |  |  |  |  | 75 |  |  |  |  | 80 |
| --- | --- | --- | --- | --- | --- | --- | --- | --- | --- | --- | --- | --- | --- | --- | --- | --- | --- | --- | --- |
| Ser | Val | Asn | Asn | Cys<br>85 | Val | Cys | His | Phe | Ser<br>90 | Pro | Leu | Lys | Ser | Asp<br>95 | Gln |
| Asp | Tyr | Ile | Leu<br>100 | Lys | Glu | Gly | Asp | Leu | Val<br>105 | Lys | Ile | Asp | Leu<br>110 | Gly | Val |
| His | Val | Asp<br>115 | Gly | Phe | Ile | Ala | Asn<br>120 | Val | Ala | His | Thr | Phe<br>125 | Val | Val | Asp |
| Val | Ala<br>130 | Gln | Gly | Thr | Gln<br>135 | Val | Thr | Gly | Arg | Lys<br>140 | Ala | Asp | Val | Ile | Lys |
| Ala<br>145 | Ala | His | Leu | Cys | Ala<br>150 | Glu | Ala | Ala | Leu | Arg<br>155 | Leu | Val | Lys | Pro | Gly<br>160 |
| Asn | Gln | Asn | Thr | Gln<br>165 | Val | Thr | Glu | Ala | Trp<br>170 | Asn | Lys | Val | Ala | His<br>175 | Ser |
| Phe | Asn | Cys | Thr<br>180 | Pro | Ile | Glu | Gly | Met<br>185 | Leu | Ser | His | Gln | Leu<br>190 | Lys | Gln |
| His | Val | Ile<br>195 | Asp | Gly | Glu | Lys | Thr<br>200 | Ile | Ile | Gln | Asn | Pro<br>205 | Thr | Asp | Gln |
| Gln | Lys<br>210 | Lys | Asp | His | Glu<br>215 | Lys | Ala | Glu | Phe | Glu<br>220 | Val | His | Glu | Val | Tyr |
| Ala<br>225 | Val | Asp | Val | Leu | Val<br>230 | Ser | Ser | Gly | Glu | Gly<br>235 | Lys | Ala | Lys | Asp | Ala<br>240 |
| Gly | Gln | Arg | Thr | Thr<br>245 | Ile | Tyr | Lys | Arg | Asp<br>250 | Pro | Ser | Lys | Gln | Tyr<br>255 | Gly |
| Leu | Lys | Met | Lys<br>260 | Thr | Ser | Arg | Ala | Phe<br>265 | Phe | Ser | Glu | Val | Glu<br>270 | Arg | Arg |
| Phe | Asp | Ala<br>275 | Met | Pro | Phe | Thr | Leu<br>280 | Arg | Ala | Phe | Glu | Asp<br>285 | Glu | Lys | Lys |
| Ala | Arg<br>290 | Met | Gly | Val | Val | Glu<br>295 | Cys | Ala | Lys | His | Glu<br>300 | Leu | Leu | Gln | Pro |
| Phe<br>305 | Asn | Val | Leu | Tyr | Glu<br>310 | Lys | Glu | Gly | Glu | Phe<br>315 | Val | Ala | Gln | Phe | Lys<br>320 |
| Phe | Thr | Val | Leu | Leu<br>325 | Met | Pro | Asn | Gly | Pro<br>330 | Met | Arg | Ile | Thr | Ser<br>335 | Gly |
| Pro | Phe | Glu | Pro<br>340 | Asp | Leu | Tyr | Lys | Ser<br>345 | Glu | Met | Glu | Val | Gln<br>350 | Asp | Ala |
| Glu | Leu | Lys<br>355 | Ala | Leu | Leu | Gln | Ser<br>360 | Ser | Ala | Ser | Arg | Lys<br>365 | Thr | Gln | Lys |
| Lys | Lys<br>370 | Lys | Lys | Lys | Ala | Ser<br>375 | Lys | Thr | Ala | Glu | Asn<br>380 | Ala | Thr | Ser | Gly |
| Glu<br>385 | Thr | Leu | Glu | Glu | Asn<br>390 | Glu | Ala | Gly | Asp |  |  |  |  |  |  |

(2) INFORMATION FOR SEQ ID NO:6:

(i) SEQUENCE CHARACTERISTICS:
        (A) LENGTH: 1456 base pairs
        (B) TYPE: nucleic acid
        (C) STRANDEDNESS: single
        (D) TOPOLOGY: linear (vii) IMMEDIATE SOURCE:
        (A) LIBRARY: ZNDANOT01
        (B) CLONE: 2458438

(xi) SEQUENCE DESCRIPTION: SEQ ID NO:6:

| TGCGCCTCAG | CCCGCGCGCT | CGCAGCTTCT | CGCTCTCGCC | TGCCTGCCCG | CTCCCTTGCT | 60 |
| --- | --- | --- | --- | --- | --- | --- |
| TGCTCGCGCT | TTCGCTCGCC | CTCTCCTCGA | GGATCGAGGG | GACTCTGACC | ACAGCCTGTG | 120 |

-continued

```
GCTGGGAAGG  GAGACAGAGG  CGGCGGCGGC  TCAGGGGAAA  CGAGGCTGCA  GTGGTGGTAG   180
TAGGAAGATG  TCGGGCGAGG  ACGAGCAACA  GGAGCAAACT  ATCGCTGAGG  ACCTGGTCGT   240
GACCAAGTAT  AAGATGGGGG  GCGACATCGC  CAACAGGGTA  CTTCGGTCCT  TGGTGGAAGC   300
ATCTAGCTCA  GGTGTGTCGG  TATTGAGCCT  GTGTGAGAAA  GGTGATGCCA  TGATTATGGA   360
AGAAACAGGG  AAAATCTTCA  AGAAAGAAAA  GGAAATGAAG  AAAGGTATTG  CTTTTCCCAC   420
CAGCATTTCG  GTAAATAACT  GTGTATGTCA  CTTCTCCCCT  TTGAAGAGCG  ACCAGGATTA   480
TATTCTCAAG  GAAGGTGACT  TGGTAAAAAT  TGACCTTGGG  GTCCATGTGG  ATGGCTTCAT   540
CGCTAATGTA  GCTCACACTT  TTGTGGTTGA  TGTAGCTCAG  GGGACCCAAG  TAACAGGGAG   600
GAAAGCAGAT  GTTATTAAGG  CAGCTCACCT  TTGTGCTGAA  GCTGCCCTAC  GCCTGGTCAA   660
ACCTGGAAAT  CAGAACACAC  AAGTGACAGA  AGCCTGGAAC  AAAGTTGCCC  ACTCATTTAA   720
CTGCACGCCA  ATAGAAGGTA  TGCTGTCACA  CCAGTTGAAG  CAGCATGTCA  TCGATGGAGA   780
AAAAACCATT  ATCCAGAATC  CCACAGACCA  GCAGAAGAAG  GACCATGAAA  AAGCTGAATT   840
TGAGGTACAT  GAAGTATATG  CTGTGGATGT  TCTCGTCAGC  TCAGGAGAGG  GCAAGGCCAA   900
GGATGCAGGA  CAGAGAACCA  CTATTTACAA  ACGAGACCCC  TCTAAACAGT  ATGGACTGAA   960
AATGAAAACT  TCACGTGCCT  TCTTCAGTGA  GGTGGAAAGG  CGTTTTGATG  CCATGCCGTT  1020
TACTTTAAGA  GCATTTGAAG  ATGAGAAGAA  GGCTCGGATG  GGTGTGGTGG  AGTGCGCCAA  1080
ACATGAACTG  CTGCAACCAT  TTAATGTTCT  CTATGAGAAG  GAGGGTGAAT  TTGTTGCCCA  1140
GTTTAAATTT  ACAGTTCTGC  TCATGCCCAA  TGGCCCCATG  CGGATAACCA  GTGGTCCCTT  1200
CGAGCCTGAC  CTCTACAAGT  CTGAGATGGA  GGTCCAGGAT  GCAGAGCTAA  AGGCCCTCCT  1260
CCAGAGTTCT  GCAAGTCGAA  AAACCCAGAA  AAAGAAAAAA  AAGAAGGCCT  CCAAGACTGC  1320
AGAGAATGCC  ACCAGTGGGG  AAACATTAGA  AGAAAATGAA  GCTGGGGACT  GAGGTGGGTC  1380
CCATCTCCCC  AGCTTGCTGC  TCCTGCCTCA  TCCCCTTCCC  ACCATACCCC  AGACTCTGTG  1440
AAGGCAGTTT  TTCTCC                                                    1456
```

(2) INFORMATION FOR SEQ ID NO:7:

(i) SEQUENCE CHARACTERISTICS:
        (A) LENGTH: 478 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 51203

(xi) SEQUENCE DESCRIPTION: SEQ ID NO:7:

```
Met  Asp  His  Ser  Leu  Gly  Trp  Gln  Gly  Asn  Ser  Val  Pro  Glu  Asp  Gly
 1             5                    10                       15

Thr  Glu  Ala  Gly  Ile  Lys  His  Phe  Leu  Glu  Asp  Ser  Ser  Asp  Asp  Ala
            20                       25                       30

Glu  Leu  Ser  Lys  Phe  Val  Lys  Asp  Phe  Pro  Gly  Ser  Glu  Pro  Tyr  His
        35                       40                       45

Ser  Ala  Glu  Ser  Lys  Thr  Arg  Val  Ala  Arg  Pro  Gln  Ile  Leu  Glu  Pro
    50                       55                       60

Arg  Pro  Gln  Ser  Pro  Asp  Leu  Cys  Asp  Asp  Val  Glu  Phe  Arg  Gly
65                       70                       75                       80

Ser  Leu  Trp  Pro  Gln  Pro  Ser  Asp  Ser  Gln  Gln  Tyr  Phe  Ser  Ala  Pro
                    85                       90                       95
```

| | | | | | | | | | | | | | | |
|---|---|---|---|---|---|---|---|---|---|---|---|---|---|---|
| Ala | Pro | Leu | Ser<br>100 | Pro | Ser | Ser | Arg | Pro<br>105 | Arg | Ser | Pro | Trp | Gly<br>110 | Lys | Leu |
| Asp | Pro | Tyr<br>115 | Asp | Ser | Ser | Glu | Asp<br>120 | Asp | Lys | Glu | Tyr | Val<br>125 | Gly | Phe | Ala |
| Thr | Leu<br>130 | Pro | Asn | Gln | Val | His<br>135 | Arg | Lys | Ser | Val | Lys<br>140 | Lys | Gly | Phe | Asp |
| Phe<br>145 | Thr | Leu | Met | Val | Ala<br>150 | Gly | Glu | Ser | Gly | Leu<br>155 | Gly | Lys | Ser | Thr | Leu<br>160 |
| Val | Asn | Ser | Leu | Phe<br>165 | Leu | Thr | Asp | Leu | Tyr<br>170 | Arg | Asp | Arg | Lys | Leu<br>175 | Leu |
| Gly | Ala | Glu | Glu<br>180 | Arg | Ile | Met | Gln | Thr<br>185 | Val | Glu | Ile | Thr | Lys<br>190 | His | Ala |
| Val | Asp | Ile<br>195 | Glu | Glu | Lys | Gly | Val<br>200 | Arg | Leu | Arg | Leu | Thr<br>205 | Ile | Val | Asp |
| Thr | Pro<br>210 | Gly | Phe | Gly | Asp | Ala<br>215 | Val | Asn | Asn | Thr | Glu<br>220 | Cys | Trp | Lys | Pro |
| Val<br>225 | Ala | Glu | Tyr | Ile | Asp<br>230 | Gln | Gln | Phe | Glu | Gln<br>235 | Tyr | Phe | Arg | Asp | Glu<br>240 |
| Ser | Gly | Leu | Asn | Arg<br>245 | Lys | Asn | Ile | Gln | Asn<br>250 | Arg | Val | His | Cys<br>255 | Cys |
| Leu | Tyr | Phe | Ile<br>260 | Ser | Pro | Phe | Gly | His<br>265 | Gly | Leu | Arg | Pro<br>270 | Leu | Asp | Val |
| Glu | Phe | Met<br>275 | Lys | Ala | Leu | His | Gln<br>280 | Arg | Val | Asn | Ile | Val<br>285 | Pro | Ile | Leu |
| Ala | Lys<br>290 | Ala | Asp | Thr | Leu | Thr<br>295 | Pro | Pro | Glu | Val | Asp<br>300 | Arg | Lys | Lys | Cys |
| Lys<br>305 | Ile | Arg | Glu | Glu | Ile<br>310 | Glu | His | Phe | Gly | Ile<br>315 | Lys | Ile | Tyr | Gln | Phe<br>320 |
| Pro | Asp | Cys | Asp | Ser<br>325 | Asp | Glu | Asp | Glu<br>330 | Asp | Phe | Lys | Leu | Gln<br>335 | Asp | Gln |
| Ala | Leu | Lys | Glu<br>340 | Ser | Ile | Pro | Phe | Ala<br>345 | Val | Ile | Gly | Ser | Asn<br>350 | Thr | Val |
| Val | Glu | Ala<br>355 | Arg | Gly | Arg | Arg | Val<br>360 | Arg | Gly | Arg | Leu | Tyr<br>365 | Pro | Trp | Gly |
| Ile | Val<br>370 | Glu | Val | Glu | Asn | Pro<br>375 | Gly | His | Cys | Asp | Phe<br>380 | Val | Lys | Leu | Arg |
| Thr<br>385 | Met | Leu | Val | Arg | Thr<br>390 | His | Met | Gln | Asp | Leu<br>395 | Lys | Asp | Val | Thr | Arg<br>400 |
| Glu | Thr | His | Tyr | Glu<br>405 | Asn | Tyr | Arg | Ala | Gln<br>410 | Cys | Ile | Gln | Ser | Met<br>415 | Thr |
| Arg | Leu | Val | Val<br>420 | Lys | Glu | Arg | Asn | Arg<br>425 | Asn | Lys | Leu | Thr | Arg<br>430 | Glu | Ser |
| Gly | Thr | Asp<br>435 | Phe | Pro | Ile | Pro | Ala<br>440 | Val | Pro | Pro | Gly | Thr<br>445 | Asp | Pro | Glu |
| Thr | Glu<br>450 | Lys | Leu | Ile | Arg | Glu<br>455 | Lys | Asp | Glu | Glu | Leu<br>460 | Arg | Arg | Met | Gln |
| Glu<br>465 | Met | Leu | His | Lys | Ile<br>470 | Gln | Arg | Gln | Met | Lys<br>475 | Glu | Thr | His | | |

( 2 ) INFORMATION FOR SEQ ID NO:8:

( i ) SEQUENCE CHARACTERISTICS:
        ( A ) LENGTH: 369 amino acids
        ( B ) TYPE: amino acid
        ( C ) STRANDEDNESS: single
        ( D ) TOPOLOGY: linear ( v i i ) IMMEDIATE SOURCE:
  ( A ) LIBRARY: GenBank
  ( B ) CLONE: 1829317

( x i ) SEQUENCE DESCRIPTION: SEQ ID NO:8:

| Met | Ser | Thr | Gly | Leu | Arg | Tyr | Lys | Ser | Lys | Leu | Ala | Thr | Pro | Glu | Asp |
|---|---|---|---|---|---|---|---|---|---|---|---|---|---|---|---|
| 1 | | | | 5 | | | | | 10 | | | | | 15 | |
| Lys | Gln | Asp | Ile | Asp | Lys | Gln | Tyr | Val | Gly | Phe | Ala | Thr | Leu | Pro | Asn |
| | | | 20 | | | | 25 | | | | | | 30 | | |
| Gln | Val | His | Arg | Lys | Ser | Val | Lys | Gly | Phe | Asp | Phe | Thr | Leu | Met | |
| | | 35 | | | | 40 | | | | | 45 | | | | |
| Val | Ala | Gly | Glu | Ser | Gly | Leu | Gly | Lys | Ser | Thr | Leu | Val | His | Ser | Leu |
| | 50 | | | | | 55 | | | | | 60 | | | | |
| Phe | Leu | Thr | Asp | Leu | Tyr | Lys | Asp | Arg | Lys | Leu | Leu | Ser | Ala | Glu | Glu |
| 65 | | | | | 70 | | | | 75 | | | | | | 80 |
| Arg | Ile | Ser | Gln | Thr | Val | Glu | Ile | Leu | Lys | His | Thr | Val | Asp | Ile | Glu |
| | | | | 85 | | | | | 90 | | | | | 95 | |
| Glu | Lys | Gly | Val | Lys | Leu | Lys | Leu | Thr | Ile | Val | Asp | Thr | Pro | Gly | Phe |
| | | | | 100 | | | | 105 | | | | | 110 | | |
| Gly | Asp | Ala | Val | Asn | Asn | Thr | Glu | Cys | Trp | Lys | Pro | Ile | Thr | Asp | Tyr |
| | | | 115 | | | | 120 | | | | | 125 | | | |
| Val | Asp | Gln | Gln | Phe | Glu | Gln | Tyr | Phe | Arg | Asp | Glu | Ser | Gly | Leu | Asn |
| | | 130 | | | | | 135 | | | | | 140 | | | |
| Arg | Lys | Asn | Ile | Gln | Asp | Asn | Arg | Val | His | Cys | Cys | Leu | Tyr | Phe | Ile |
| 145 | | | | | 150 | | | | | 155 | | | | | 160 |
| Ser | Pro | Phe | Gly | His | Gly | Leu | Arg | Pro | Val | Asp | Val | Gly | Phe | Met | Lys |
| | | | | 165 | | | | | 170 | | | | | 175 | |
| Ala | Leu | His | Glu | Lys | Val | Asn | Ile | Val | Pro | Leu | Ile | Ala | Lys | Ala | Asp |
| | | | 180 | | | | | 185 | | | | | 190 | | |
| Cys | Leu | Val | Pro | Ser | Glu | Ile | Arg | Lys | Leu | Lys | Glu | Arg | Ile | Arg | Glu |
| | | | 195 | | | | | 200 | | | | | 205 | | |
| Glu | Ile | Asp | Lys | Phe | Gly | Ile | His | Val | Tyr | Gln | Phe | Pro | Glu | Cys | Asp |
| | 210 | | | | | 215 | | | | | 220 | | | | |
| Ser | Asp | Glu | Asp | Glu | Asp | Phe | Lys | Gln | Gln | Asp | Arg | Glu | Leu | Lys | Glu |
| 225 | | | | | 230 | | | | | 235 | | | | | 240 |
| Ser | Ala | Pro | Phe | Ala | Val | Ile | Gly | Ser | Asn | Thr | Val | Val | Glu | Ala | Lys |
| | | | | 245 | | | | | 250 | | | | | 255 | |
| Gly | Gln | Arg | Val | Arg | Gly | Arg | Leu | Tyr | Pro | Trp | Gly | Ile | Val | Glu | Val |
| | | | 260 | | | | | 265 | | | | | 270 | | |
| Glu | Asn | Gln | Ala | His | Cys | Asp | Phe | Val | Lys | Leu | Arg | Asn | Met | Leu | Ile |
| | | 275 | | | | | 280 | | | | | 285 | | | |
| Arg | Thr | His | Met | His | Asp | Leu | Lys | Asp | Val | Thr | Cys | Asp | Val | His | Tyr |
| | 290 | | | | | 295 | | | | | 300 | | | | |
| Glu | Asn | Tyr | Arg | Ala | His | Cys | Ile | Gln | Gln | Met | Thr | Ser | Lys | Leu | Thr |
| 305 | | | | | 310 | | | | | 315 | | | | | 320 |
| Gln | Asp | Ser | Arg | Met | Glu | Ser | Pro | Ile | Pro | Ile | Leu | Pro | Leu | Pro | Thr |
| | | | | 325 | | | | 330 | | | | | 335 | | |
| Pro | Asp | Ala | Glu | Thr | Glu | Lys | Leu | Ile | Arg | Met | Lys | Asp | Glu | Glu | Leu |
| | | | 340 | | | | | 345 | | | | | 350 | | |
| Arg | Arg | Met | Gln | Glu | Met | Leu | Gln | Arg | Met | Lys | Gln | Gln | Met | Gln | Asp |
| | | 355 | | | | | 360 | | | | | 365 | | | |
| Gln | | | | | | | | | | | | | | | |

( 2 ) INFORMATION FOR SEQ ID NO:9:

(i) SEQUENCE CHARACTERISTICS:
  (A) LENGTH: 424 amino acids
  (B) TYPE: amino acid
  (C) STRANDEDNESS: single
  (D) TOPOLOGY: linear (vii) IMMEDIATE SOURCE:
  (A) LIBRARY: GenBank
  (B) CLONE: 1469179

(xi) SEQUENCE DESCRIPTION: SEQ ID NO:9:

```
Thr  Asp  Ile  Ala  Arg  Gln  Val  Gly  Glu  Gly  Cys  Arg  Thr  Val  Pro  Leu
 1                    5                   10                        15

Ala  Gly  His  Val  Gly  Phe  Asp  Ser  Leu  Pro  Asp  Gln  Leu  Val  Asn  Lys
              20                        25                   30

Ser  Val  Ser  Gln  Gly  Phe  Cys  Phe  Asn  Ile  Leu  Cys  Val  Gly  Glu  Thr
          35                        40                        45

Gly  Leu  Gly  Lys  Ser  Thr  Leu  Met  Asp  Thr  Leu  Phe  Asn  Thr  Lys  Phe
 50                        55                        60

Glu  Gly  Glu  Pro  Ala  Thr  His  Thr  Gln  Pro  Gly  Val  Gln  Leu  Gln  Ser
 65                        70                   75                        80

Asn  Thr  Tyr  Asp  Leu  Gln  Glu  Ser  Asn  Val  Arg  Leu  Lys  Leu  Thr  Ile
                    85                        90                        95

Val  Ser  Thr  Val  Gly  Phe  Gly  Asp  Gln  Ile  Asn  Lys  Glu  Asp  Ser  Tyr
              100                       105                       110

Lys  Pro  Ile  Val  Glu  Phe  Ile  Asp  Ala  Gln  Phe  Glu  Ala  Tyr  Leu  Gln
          115                       120                       125

Glu  Glu  Leu  Lys  Ile  Arg  Arg  Val  Leu  His  Thr  Tyr  His  Asp  Ser  Arg
      130                       135                       140

Ile  His  Val  Cys  Leu  Tyr  Phe  Ile  Ala  Pro  Thr  Gly  His  Ser  Leu  Lys
145                       150                       155                      160

Ser  Leu  Asp  Leu  Val  Thr  Met  Lys  Lys  Leu  Asp  Ser  Lys  Val  Asn  Ile
              165                       170                       175

Ile  Pro  Ile  Ile  Ala  Lys  Ala  Asp  Ala  Ile  Ser  Lys  Ser  Glu  Leu  Thr
              180                       185                       190

Lys  Phe  Lys  Ile  Lys  Ile  Thr  Ser  Glu  Leu  Val  Ser  Asn  Gly  Val  Gln
          195                       200                       205

Ile  Tyr  Gln  Phe  Pro  Thr  Asp  Asp  Glu  Ser  Val  Ala  Glu  Ile  Asn  Gly
      210                       215                       220

Thr  Met  Asn  Ala  His  Leu  Pro  Phe  Ala  Val  Ile  Gly  Ser  Thr  Glu  Glu
225                       230                       235                      240

Leu  Lys  Ile  Gly  Asn  Lys  Met  Met  Arg  Ala  Arg  Gln  Tyr  Pro  Trp  Gly
                    245                       250                       255

Thr  Val  Gln  Val  Glu  Asn  Glu  Ala  His  Cys  Asp  Phe  Val  Lys  Leu  Arg
              260                       265                       270

Glu  Met  Leu  Ile  Arg  Val  Asn  Met  Glu  Asp  Leu  Arg  Glu  Gln  Thr  His
          275                       280                       285

Thr  Arg  His  Tyr  Glu  Leu  Tyr  Arg  Arg  Cys  Lys  Leu  Glu  Glu  Met  Gly
      290                       295                       300

Phe  Lys  Asp  Thr  Asp  Pro  Asp  Ser  Lys  Pro  Phe  Ser  Leu  Gln  Glu  Thr
305                       310                       315                      320

Tyr  Glu  Ala  Lys  Arg  Asn  Glu  Phe  Leu  Gly  Glu  Leu  Gln  Lys  Lys  Glu
                    325                       330                       335

Glu  Glu  Met  Arg  Gln  Met  Phe  Val  Gln  Arg  Val  Lys  Glu  Lys  Glu  Ala
              340                       345                       350

Glu  Leu  Lys  Glu  Ala  Glu  Lys  Glu  Leu  His  Glu  Lys  Phe  Asp  Arg  Leu
```

|     |     |     |     | 355 |     |     |     |     | 360 |     |     |     |     | 365 |     |
| --- | --- | --- | --- | --- | --- | --- | --- | --- | --- | --- | --- | --- | --- | --- | --- |

Lys Lys Leu His Gln Asp Glu Lys Lys Leu Glu Asp Lys Lys Lys
370                     375                     380

Ser Leu Asp Asp Glu Val Asn Ala Phe Lys Gln Arg Lys Thr Ala Ala
385                 390                 395                 400

Glu Leu Leu Gln Ser Gln Gly Ser Gln Ala Gly Gly Ser Gln Thr Leu
            405                 410                 415

Lys Arg Asp Lys Glu Lys Lys Asn
            420

( 2 ) INFORMATION FOR SEQ ID NO:10:

( i ) SEQUENCE CHARACTERISTICS:
        ( A ) LENGTH: 394 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: GenBank
        ( B ) CLONE: 1167967

( x i ) SEQUENCE DESCRIPTION: SEQ ID NO:10:

Met Ser Gly Glu Asp Glu Gln Gln Glu Gln Thr Ile Ala Glu Asp Leu
1               5                   10                  15

Val Val Thr Lys Tyr Lys Met Gly Gly Asp Ile Ala Asn Arg Val Leu
            20                  25                  30

Arg Ser Leu Val Glu Ala Ser Ser Ser Gly Val Ser Val Leu Ser Leu
            35                  40                  45

Cys Glu Lys Gly Asp Ala Met Ile Met Glu Glu Thr Gly Lys Ile Phe
    50                  55                  60

Lys Lys Glu Lys Glu Met Lys Lys Gly Ile Ala Phe Pro Thr Ser Ile
65                  70                  75                  80

Ser Val Asn Asn Cys Val Cys His Phe Ser Pro Leu Lys Ser Asp Gln
                85                  90                  95

Asp Tyr Ile Leu Lys Glu Gly Asp Leu Val Lys Ile Asp Leu Gly Val
            100                 105                 110

His Val Asp Gly Phe Ile Ala Asn Val Ala His Thr Phe Val Ile Gly
            115                 120                 125

Val Ala Gln Gly Thr Gln Val Thr Gly Arg Lys Ala Asp Val Ile Lys
    130                 135                 140

Ala Ala His Leu Cys Ala Glu Ala Ala Leu Arg Leu Val Lys Pro Gly
145                 150                 155                 160

Asn Gln Asn Thr Gln Val Thr Glu Ala Trp Asn Lys Val Ala His Ser
            165                 170                 175

Phe Asn Cys Thr Pro Ile Glu Gly Met Leu Ser His Gln Leu Lys Gln
            180                 185                 190

His Val Ile Asp Gly Glu Lys Thr Ile Ile Gln Asn Pro Thr Asp Gln
        195                 200                 205

Gln Lys Lys Asp His Glu Lys Ala Glu Phe Glu Val His Glu Val Tyr
    210                 215                 220

Ala Val Asp Val Leu Val Ser Ser Gly Glu Gly Lys Ala Lys Asp Ala
225                 230                 235                 240

Gly Gln Arg Thr Thr Ile Tyr Lys Arg Asp Pro Ser Lys Gln Tyr Gly
            245                 250                 255

Leu Lys Met Lys Thr Ser Arg Ala Phe Phe Ser Glu Val Glu Arg Arg
            260                 265                 270

-continued

| Phe | Asp | Ala 275 | Met | Pro | Phe | Thr | Leu 280 | Arg | Ala | Phe | Glu | Asp 285 | Glu | Lys | Lys |
| Ala | Arg 290 | Met | Gly | Val | Val | Glu 295 | Cys | Ala | Lys | His | Glu 300 | Leu | Leu | Gln | Pro |
| Phe 305 | Asn | Val | Leu | Tyr | Glu 310 | Lys | Glu | Gly | Glu | Phe 315 | Val | Ala | Gln | Phe | Lys 320 |
| Phe | Thr | Val | Leu | Leu 325 | Met | Pro | Asn | Gly | Pro 330 | Met | Arg | Ile | Thr | Ser 335 | Gly |
| Pro | Phe | Glu | Pro 340 | Asp | Leu | Tyr | Lys | Ser 345 | Glu | Met | Glu | Val | Gln 350 | Asp | Ala |
| Glu | Leu | Lys 355 | Ala | Leu | Leu | Gln | Ser 360 | Ser | Ala | Ser | Arg | Lys 365 | Thr | Gln | Lys |
| Lys | Lys 370 | Lys | Lys | Lys | Ala | Ser 375 | Lys | Thr | Val | Glu | Asn 380 | Ala | Thr | Ser | Gly |
| Glu 385 | Thr | Leu | Glu | Glu | Asn 390 | Gly | Ala | Gly | Asp | | | | | | |